(12) United States Patent
Brugel et al.

(10) Patent No.: US 7,449,474 B2
(45) Date of Patent: Nov. 11, 2008

(54) TRI-SUBSTITUTED UREAS AS CYTOKINE INHIBITORS

(75) Inventors: Todd Andrew Brugel, West Chester, OH (US); Jennifer Anne Townes, Loveland, OH (US); Michael Philip Clark, Maineville, OH (US); Mark Sabat, Loveland, OH (US); Adam Golebiowski, Loveland, OH (US); Biswanath De, Cincinnati, OH (US); Stephen Matthew Berberich, Alexandria, OH (US); Gregory Kent Bosch, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 566 days.

(21) Appl. No.: 11/111,581

(22) Filed: Apr. 21, 2005

(65) Prior Publication Data

US 2005/0239811 A1 Oct. 27, 2005

Related U.S. Application Data

(60) Provisional application No. 60/564,745, filed on Apr. 22, 2004.

(51) Int. Cl.
*C07D 239/48* (2006.01)
*A61K 31/506* (2006.01)
(52) U.S. Cl. ...................... 514/275; 544/323
(58) Field of Classification Search ................ 544/323; 514/275
See application file for complete search history.

(56) References Cited

FOREIGN PATENT DOCUMENTS

WO WO 99/23091 A1 5/1999

OTHER PUBLICATIONS

Robinson, Medical Therapy of Inflammatory Bowel Disease for the 21st Century, Eur J Surg 1998; Suppl 582, pp. 90-98.*
Aleman et al., PubMed Abstract (Antivir Ther. 4(2):109-15), 1999.*
Rasmussen, PubMed Abstract (Dan Med Bull. 47(2):94-114), 2000.*
Green et al., PubMed Abstract (Immunol Rev 169:11-22), 1999.*
Van Deventer, PubMed Abstract (Intensive Care Med. 26 Suppl 1:S98-102), 2000.*
Holzheimer, PubMed Abstract (J Chemother. 13 Spec No. 1(1): 159-72), 2001.*
Lesher, George Y., et al., "Novel orally active inhibitors of passive cutaneous anaphylaxis in rats: N-[2-(4-pyridinyl)-4-pyrimidinyl]ureas and dialkyl[[2-(4-pyridinyl)-4-pyrimidinyl]amino]methyler," Journal of Medical Chemistry, 25(7), 837-42. 1982, p. 841; Table IV.

* cited by examiner

*Primary Examiner*—Deepak Rao
(74) *Attorney, Agent, or Firm*—Kelly L. McDow; Andrew A. Paul

(57) ABSTRACT

The present invention relates to 1,1,3-tri-substituted ureas which inhibit the extracellular release of inflammatory cytokines, said cytokines responsible for one or more human or higher mammalian disease states. The present invention further relates to compositions comprising said 1,1,3-tri-substituted ureas which inhibit the extracellular release of inflammatory cytokines, and methods for preventing, abating, or otherwise controlling enzymes which are understood to be the active components responsible for the herein described disease states.

13 Claims, No Drawings

TRI-SUBSTITUTED UREAS AS CYTOKINE INHIBITORS

CROSS REFERENCE TO RELATED APPLICATIONS

This application claims priority under Title 35, United States Code 119(e) from Provisional Application Ser. No. 60/564,745, filed Apr. 22, 2004.

FIELD OF THE INVENTION

The present invention relates to 1-(N-substituted aryl)-1-N-(2-substituted pyrimidin-4-yl)-3-N-(alkyl or substituted alkyl) ureas which inhibit the extracellular release of inflammatory cytokines, said cytokines responsible for one or more human or higher mammalian disease states. The present invention further relates to compositions comprising said N-1,1,3-tri-substituted ureas and methods for preventing, abating, or otherwise controlling enzymes which are understood to be the active components responsible for the herein described disease states.

DETAILED DESCRIPTION OF THE INVENTION

The present invention addresses several unmet medical needs, inter alia;
1) Providing pharmaceutical compositions capable of effectively blocking inflammatory cytokine production from cells, which thereby allows for the mitigation, alleviation, control, abatement, retardation, or prevention of one or more disease states or syndromes which are related to the extracellular release of one or more cytokines;
   a) Affecting the release of Interleukin-1 (IL-1): implicated as the molecule responsible for a large number of disease states, inter alia, rheumatoid arthritis, osteoarthritis, as well as other disease states which relate to connective tissue degradation;
   b) Affecting inducible Cycloxygenase-2 (COX-2) expression: inhibitors of cytokine release are proposed as inhibitors of inducible COX-2 expression, which has been shown to be increased by cytokines.
2) Providing pharmaceutical compositions which are efficacious in affecting the release of Tumor Necrosis Factor-α (TNF-α): This pro-inflammatory cytokine is suggested as an important mediator in many disease states or syndromes, inter alia, rheumatoid arthritis, osteoarthritis, inflammatory bowel disease (IBD), septic shock, cardiopulmonary dysfunction, acute respiratory disease, and cachexia.
3) Providing a pharmaceutical composition which is efficacious in providing analgesia, or otherwise relieving pain in humans and higher mammals.

These and other unmet medical needs are surprisingly resolved by the compounds of the present invention, which are capable of selectively affecting one or more disease states, conditions, or syndromes caused or affected by the extracellular release of cytokines.

Although each compound will not be effective against each and every disease state affected by the extracellular release of cytokines, nevertheless, the formulator is left to selecting the compound and make-up of a pharmaceutical composition used to treat the selected condition or illness non-limiting examples of which are described herein below.

The present invention relates to 1,1,3-tri-substituted ureas, for example, 1-(3-substituted aryl)-1-(2-substituted-pyrimidin-4-yl)-3-alkyl ureas, 1-(2-substituted aryl)-1-(2-substituted-pyrimidin-4-yl)-3-alkyl ureas, 1-(2,6-disubstituted substituted aryl)-1-(2-substituted-pyrimidin-4-yl)-3-alkyl ureas, and the like which are suitable for mediating, controlling or otherwise inhibiting the extracellular release of certain cytokines, especially inflammatory cytokines, said cytokines playing a role in the stimulation, cause, or manifestation of a wide variety of diseases, disease states, or syndromes.

The following chemical hierarchy is used throughout the specification to particularly point out and distinctly claim the units which comprise the compounds of the present invention. The term "hydrocarbyl" stands for any carbon atom-based unit, said units optionally containing one or more organic functional groups, including inorganic atom comprising salts, inter alia, carboxylate salts, and quaternary ammonium salts. Encompassed within the term "hydrocarbyl" are the terms "acyclic" and "cyclic" units which divide hydrocarbyl units into cyclic and non-cyclic classes. Cyclic hydrocarbyl units include monocyclic, bicyclic, fused ring, and spirocyclic ring systems. Heterocyclic and heteroaryl units comprise one or more heteroatoms chosen from nitrogen, oxygen, sulfur, and combinations of these heteroatoms.

1. Substituted and unsubstituted $C_1$-$C_{10}$ acyclic hydrocarbyl: For the purposes of the present invention the term "substituted and unsubstituted $C_1$-$C_{10}$ acyclic hydrocarbyl" encompasses 3 categories of units:
   i) $C_1$-$C_{10}$ linear or branched alkyl, non-limiting examples of which includes, methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); substituted $C_1$-$C_{10}$ linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), and 3-carboxypropyl ($C_3$).
   ii) $C_2$-$C_{10}$ linear or branched alkenyl, non-limiting examples of which includes, ethenyl ($C_2$), 3-propenyl ($C_3$), 1-propenyl (also 2-methylethenyl) ($C_3$), isopropenyl (also 2-methylethen-2-yl) ($C_3$), and buten-4-yl ($C_4$); substituted $C_2$-$C_{10}$ linear or branched alkenyl, non-limiting examples of which includes, 2-chloroethenyl (also 2-chlorovinyl) ($C_2$), 4-hydroxybuten-1-yl ($C_4$), 7-hydroxy-7-methyloct-4-en-2-yl (Cg), and 7-hydroxy-7-methylocta-3,5-dien-2-yl ($C_9$).
   iii) $C_2$-$C_{10}$ linear or branched alkynyl, non-limiting examples of which includes, ethynyl ($C_2$), prop-2-ynyl (also propargyl) ($C_3$), propyn-1-yl ($C_3$), and 2-methyl-hex-4-yn-1-yl ($C_7$); substituted $C_2$-$C_{10}$ linear or branched alkynyl, non-limiting examples of which includes, 5-hydroxy-5-methylhex-3-ynyl ($C_7$), 6-hydroxy-6-methylhept-3-yn-2-yl ($C_8$), and 5-hydroxy-5-ethylhept-3-ynyl ($C_9$).

2. Substituted and unsubstituted $C_1$-$C_{10}$ cyclic hydrocarbyl: For the purposes of the present invention the term "substituted and unsubstituted $C_1$-$C_{10}$ cyclic hydrocarbyl" encompasses 5 categories of units:
   i) $C_3$-$C_{10}$ carbocyclic units, non-limiting examples of which include, cyclopropyl ($C_3$), cyclobutyl ($C_4$), cyclopentyl ($C_5$), cyclohexyl ($C_6$), cycloheptyl ($C_7$), decalinyl ($C_{10}$), and decahydro-azulenyl ($C_{10}$); substituted $C_3$-$C_{10}$ carbocyclic units, non-limiting examples of which includes, 2-methylcyclopropyl ($C_3$), 2,5-dimethylcyclopentyl ($C_5$), 4-tert-butylcyclopentyl ($C_5$), 3,5-dichlorocyclohexyl ($C_6$), and 4-hydroxy-cyclohexyl ($C_6$).
   ii) $C_6$-$C_{10}$ aryl units which include, phenyl, naphthen-1-yl, and naphthen-2-yl; substituted $C_6$-$C_{10}$ aryl units, non-limiting examples of which includes, 4-fluorophenyl ($C_6$), 2,6-di-tert-butylphenyl ($C_6$), 3-hydroxyphenyl ($C_6$), 8-hydroxynaphthylen-2-yl ($C_{10}$), and 6-cyano-naphthylen-1-yl ($C_{10}$).

iii) $C_1$-$C_{10}$ heterocyclic units, which are heterocyclic units containing from 1 to 10 carbon atoms and one or more heteroatoms chosen from nitrogen, oxygen, sulfur, and mixtures thereof; non-limiting examples of which include, 1,2,3,4-tetrazolyl ($C_1$), aziridinyl ($C_2$), oxazolyl ($C_3$), tetrahydrofuranyl ($C_4$), dihydropyranyl ($C_5$), piperidin-2-one (valerolactam) ($C_5$), 2,3,4,5-tetrahydro-1H-azepinyl ($C_6$), 2,3-dihydro-1H-indole ($C_8$), and 1,2,3,4-tetrahydroquinoline ($C_9$); substituted $C_1$-$C_{10}$ heterocyclic units, non-limiting examples of which include, 2-amino-4,5-dihydro-3H-pyrrolyl ($C_4$), N-methylmorpholinyl ($C_4$), 2,6-dimethylpiperazinyl ($C_4$), and, 1-aza-bicyclo[2.2.2]octane.

iv) $C_1$-$C_{10}$ heteroaryl units, which are heteroaryl units containing from 1 to 10 carbon atoms and one or more heteroatoms chosen from nitrogen, oxygen, sulfur, and mixtures thereof; non-limiting examples of which include, triazinyl ($C_3$), furanyl ($C_4$), thiophenyl ($C_4$), pyrimidinyl ($C_4$), pyridinyl ($C_5$), and 6,7-dihydro-5H-cyclopenta[b]pyridine ($C_8$); substituted $C_1$-$C_{10}$ heteroaryl units, non-limiting examples of which include, 4-dimethylaminopyridinyl ($C_5$) and 2-methylindolyl ($C_8$).

The substituted and unsubstituted $C_1$-$C_{10}$ cyclic hydrocarbyl units of the present invention can be bonded directly to the core pyrimidinyl-urea scaffold:

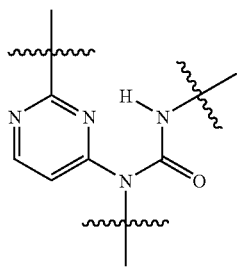

or they can be bonded to the core scaffold by way of a linking unit (tethered units) described herein below. Linked or tethered units include alkylenearyl units which are aryl units bonded to the core scaffold by way of an alkylene unit, for example, benzyl units having the formula:

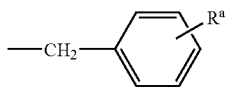

or alkyleneheteroaryl units for example a 2-picolyl unit having the formula:

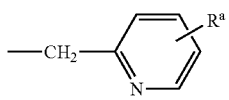

wherein $R^a$ represents one or more optional substitutions for the aryl ring hydrogen atoms. Non-limiting examples of substituted and unsubstituted $C_6$-$C_{10}$ alkylenearyl units include 2-methylbenzyl ($C_6$), 3-N,N-dimethylaminobenzyl ($C_6$), 4-fluorobenzyl ($C_6$), (8-hydroxy)naphthalen-2-ylmethyl ($C_{10}$), and 2-(3-hydroxy-phenyl)ethyl ($C_6$). Non-limiting examples of substituted and unsubstituted $C_1$-$C_{10}$ alkyleneheteroaryl units include piperidin-1-ylmethyl, piperidin-4-ylmethyl, tetrahydro-pyran-4-ylmethyl, morpholin-4-ylmethyl, isoquinolin-1-ylmethyl, and imidazolin-2-ylethyl. Non-limiting examples of $C_3$-$C_{10}$ alkylenecarbocyclic units include, cyclopropylmethyl ($C_3$), cyclopentylethyl ($C_5$), and cyclohexylmethyl ($C_6$).

The term "aryloyl" as it relates to the present invention are derivatives of aryl units bonded to a carbonyl unit, aryl units include benzene and naphthalene. A non-limiting example of an aryloyl unit is a substituted or unsubstituted benzoyl unit having the general formula:

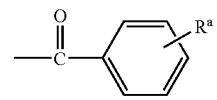

wherein $R^a$ represents one or more possible substitutions for a hydrogen atom. Heteroaryloyl units are units which are derived from heteroaryl units bonded to a carbonyl unit.

For the purposed of the present invention fused ring units, as well as spirocyclic rings, bicyclic rings and the like, which comprise a single heteroatom will be considered to belong to the cyclic family of the heteroatom containing ring. For example, 1,2,3,4-tetrahydroquinoline having the formula:

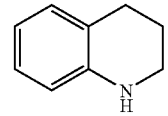

is, for the purposes of the present invention, considered a heterocyclic unit. 6,7-Dihydro-5H-[1]pyrindine having the formula:

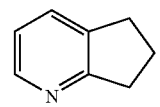

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

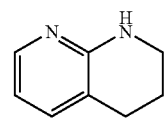

is, for the purposes of the present invention, considered a heteroaryl unit.

The term "substituted" is used throughout the specification. The term "substituted" is defined herein as "a hydrocarbyl moiety, whether acyclic or cyclic, which has one or more hydrogen atoms replaced by a substituent or several substituents as defined herein below. The units, which substituted for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit."

The following are non-limiting examples of units which can substitute for hydrogen atoms on a hydrocarbyl or other unit:
i) —$OR^8$;
ii) —$C(O)R^8$;
iii) —$C(O)OR^8$;
iv) —$C(O)N(R^8)_2$;
v) —CN;
vi) —$N(R^8)_2$;
vii) —halogen;
viii) —$CF_3$, —$CCl_3$, —$CBr_3$; and
ix) —$SO_2R^8$ wherein each $R^8$ is independently hydrogen, substituted or unsubstituted $C_1$-$C_4$ linear, branched, or cyclic alkyl; or two $R^8$ units can be taken together to form a ring comprising from 3-7 atoms.

The compounds of the present invention are 1,1,3-tri-substituted ureas having the core scaffold:

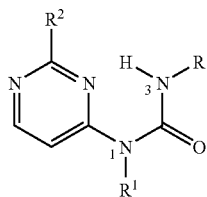

which comprises a first position nitrogen atom ($N^1$) and a third position nitrogen atom ($N^3$) on either side of a central carbonyl unit. To this core scaffold is attached at the first position nitrogen atom ($N^1$), a 2-substituted pyrimidin-4-yl unit bearing the $R^2$ units as the number 2 ring position substituent. Also attached to the first position nitrogen atom ($N^1$) is an $R^1$ unit as defined herein below. Attached to the third position nitrogen atom ($N^3$) is an R unit which is a unit as described herein below.

R units are substituted or unsubstituted $C_1$-$C_{10}$ linear or branched alkyl.

The first aspect of R relates to $C_1$-$C_4$ alkyl units chosen from methyl, ethyl, n-propyl, iso-propyl, n-butyl, sec-butyl, iso-butyl, and tert-butyl.

The second aspect of R relates to substituted $C_1$-$C_4$ alkyl units chosen from —$CH_2OH$, —$CH_2OCH_3$, —$CH_2CN$, —$CH_2CH_2OH$, —$CH_2CH_2OCH_3$, —$CH_2CH_2CH_2OH$, —$CHOH(CH_3)_2$, —$CH_2CH_2CH_2OCH_3$, —$CH_2NH_2$, and —$CH_2N(CH_3)_2$. Then preparing the compounds of the present invention which comprise R units according to the second aspect of R, it may be necessary depending upon the substituent, inter alia, hydroxyl, amino, to prepare isocyanates having a protecting group for any reactive heteroatom. For example, when R is —$CH_2OH$, an isocyanate having a protecting group present such as $OCNCH_2CH_2OBoc$ or $OCNCH_2CH_2OCbz$ may be required.

The third aspect of R relates to $C_5$-$C_{10}$ linear or methyl branched alkyl units chosen from n-pentyl, iso-pentyl, neo-pentyl, n-hexyl, n-heptyl, 2-methylhexyl, 3-methylhexyl, 4-methylhexyl, 2-methylheptyl, n-octyl, n-nonyl, and n-decyl.

$R^1$ units have the formula:

$$—(L)_x\text{-}R^3$$

wherein $R^3$ is chosen from:
i) substituted or unsubstituted $C_3$-$C_{10}$ carbocyclic;
ii) substituted or unsubstituted $C_6$-$C_{10}$ aryl;
iii) substituted or unsubstituted $C_1$-$C_{10}$ heterocyclic; and
iv) substituted or unsubstituted $C_1$-$C_{10}$ heteroaryl the index x is equal to 0 or 1, $R^3$ is a unit selected from the group consisting of:

The first aspect of $R^3$ relates to substituted or unsubstituted $C_6$ aryl units, the first iteration of which relates to units chosen from phenyl, 2-fluorophenyl, 3-fluorophenyl, 4-fluorophenyl, 4-hydroxyphenyl, 4-methoxyphenyl, 4-ethoxyphenyl, 4-methylphenyl, 4-chlorophenyl, 4-methylsulfanylphenyl, and 4-dimethylaminophenyl.

The second aspect of $R^3$ relates to substituted or unsubstituted $C_3$, $C_4$ or $C_5$ heterocyclic units, the first iteration of which relates to substituted and unsubstituted 6-member rings chosen from piperazine, piperidine, morpholine, and tetrahydropyran. The second iteration of this aspect of $R^5$ relates to 5-member rings chosen from tetrahydrofuran, pyrrolidine, and imidazolidine. The $C_3$, $C_4$ or $C_5$ heterocyclic units can be bonded to the core structure by any ring atom, for example, tetrahydrofuran-2-yl, tetrahydrofuran-3-yl, pyrrolidin-2-yl, pyrrolidin-3-yl, imidazolidine-2-yl, imidazolidine-4-yl, imidazolidine-5-yl, piperazine-1-yl, piperazine-2-yl, piperidine-1-yl, piperidine-2-yl, piperidine-3-yl, piperidine-4-yl, morpholin-4-yl, and tetrahydropyran-4-yl.

$R^2$ has the formula:

$$\text{-}(L^1)_y—R^4$$

the index y is equal to 0 or 1, $R^4$ is a unit selected from the group consisting of:
i) hydrogen;
ii) substituted or unsubstituted $C_1$-$C_{10}$ linear or branched hydrocarbyl;
iii) substituted or unsubstituted $C_3$-$C_{10}$ carbocyclic;
iv) substituted or unsubstituted $C_6$-$C_{10}$ aryl;
v) substituted or unsubstituted $C_1$-$C_{10}$ heterocyclic; and
vi) substituted or unsubstituted $C_1$-$C_{10}$ heteroaryl.

The first Category of $R^2$ relates to units which are units having an amino linking unit —NH—, said $R^2$ units having the formula:

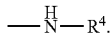

The first aspect of $R^4$ as it relates to the first category of $R^2$, includes substituted or unsubstituted $C_1$-$C_{10}$ linear or branched hydrocarbyl, the first iteration of which includes alkyl units chosen from 1(S)-2-hydroxy-1,2-dimethylpropyl, 1(S)-2-methoxy-1-methylethyl, 1(S)-sec-butyl, and iso-propyl.

The second aspect of $R^4$ relates to substituted or unsubstituted tethered $C_6$ aryl, the first iteration of which is substituted and unsubstituted phenyl and benzyl (when $R^4$ comprises a tethered cyclic hydrocarbyl). Non-limiting examples of $R^2$ units include benzyl and (1S)-phenylethyl when $L^1$ is —NH—.

The third aspect of $R^4$ as it relates to the first category of $R^2$, includes $C_1$-$C_{10}$ substituted or unsubstituted heterocycles, the first iteration of which is a substituted or unsubstituted $C_4$ or $C_5$ heterocyclic unit chosen from piperidin-1-yl, piperidin-4-yl, tetrahydropyran-4-yl, and morpholin-4-yl. The second iteration of this aspect relates to substituted or unsubstituted $C_4$ or $C_5$ heterocyclic unit tethered to the amino linking unit, —NH—, by way of a methylene unit, —CH$_2$—; non-limiting examples of this iteration are chosen from piperidin-1-ylmethyl, piperidin-4-ylmethyl, tetrahydropyran-4-ylmethyl, and morpholin-4-ylmethyl.

L and $L^1$ are linking groups each of which are independently selected from the group consisting of:
 i) —C($R^5$)$_2$—;
 ii) —N$R^5$—; and
 iii) —O—;

$R^5$ is hydrogen, $C_1$-$C_4$ alkyl; or two $R^5$ units can be taken together to form a carbonyl unit, and the indices x or y are 0 or 1. When x or y is equal to 0 the linking group is absent, when x or y is equal to 1 the linking group is present.

The first aspect of $L^1$ relates to compounds wherein $L^1$ is chosen from —C(O)—, —CH$_2$— or —NH—. A first iteration of this aspect of $L^1$ relates to Category I—first aspect; first, second, and third iterations wherein —NH— is used to link R units which are substituted or unsubstituted $C_1$-$C_{10}$ linear or branched hydrocarbyl units with the core 1,1,3-tri-substituted urea scaffold. One non-limiting example of these $R^4$ units includes a unit chosen from 1(S)-2-hydroxy-1,2-dimethylpropyl, 1(S)-2-methoxy-1-methylethyl, 1(S)-sec-butyl, and isopropyl thereby providing an $R^2$ chosen from a unit chosen from 1(S)-2-hydroxy-1,2-dimethylpropylamino, 1(S)-2-methoxy-1-methylethylamino, 1(S)-sec-butylamino, and isopropylamino.

A second aspect of $L^1$ relates to —NH— units used to link heterocyclic and heterocyclic units tethered with a methylene unit, non-limiting examples of which include piperidin-1-yl, piperidin-1-ylmethyl, piperidin-4-yl, tetrahydropyran-4-yl, tetrahydro-pyran-4-ylmethyl, morpholin-4-yl, and morpholin-4-ylmethyl.

The analogs (compounds) of the present invention are arranged into several categories to assist the formulator in applying a rational synthetic strategy for the preparation of analogs which are not expressly exampled herein. The arrangement into categories does not imply increased or decreased efficacy for any of the compositions of matter described herein.

The compounds which comprise Category I of the present invention are N-(aryl or substituted aryl)-(2-substituted-pyrimidin-4-yl)-N'-alkyl-ureas having the formula:

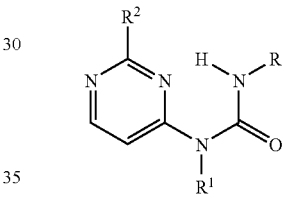

the first aspect of which relates to R units which are unsubstituted $C_1$-$C_4$ linear or branched alkyl. Non-limiting examples of $R^1$ and $R^2$ are defined herein below in Table I.

TABLE I

| No. | R | $R^1$ | $R^2$ |
|---|---|---|---|
| 1 | —CH$_3$ | 4-methoxyphenyl | 2-hydroxy-1,2-dimethyl-propylamino |
| 2 | —CH$_3$ | 4-ethoxyphenyl | 2-hydroxy-1,2-dimethyl-propylamino |
| 3 | —CH$_3$ | 4-fluorophenyl | 2-hydroxy-1,2-dimethyl-propylamino |
| 4 | —CH$_3$ | 4-methylphenyl | 2-hydroxy-1,2-dimethyl-propylamino |
| 5 | —CH$_3$ | 4-methylsulfanylphenyl | 2-hydroxy-1,2-dimethyl-propylamino |
| 6 | —CH$_3$ | 4-methoxyphenyl | 2-methoxy-1-methyl-ethylamino |
| 7 | —CH$_3$ | 4-ethoxyphenyl | 2-methoxy-1-methyl-ethylamino |
| 8 | —CH$_3$ | 4-fluorophenyl | 2-methoxy-1-methyl-ethylamino |
| 9 | —CH$_3$ | 4-methylphenyl | 2-methoxy-1-methyl-ethylamino |
| 10 | —CH$_3$ | 4-methylsulfanylphenyl | 2-methoxy-1-methyl-ethylamino |
| 11 | —CH$_3$ | 4-methoxyphenyl | 1-phenyl-ethylamino |
| 12 | —CH$_3$ | 4-ethoxyphenyl | 1-phenyl-ethylamino |
| 13 | —CH$_3$ | 4-fluorophenyl | 1-phenyl-ethylamino |
| 14 | —CH$_3$ | 4-methylphenyl | 1-phenyl-ethylamino |
| 15 | —CH$_3$ | 4-methylsulfanylphenyl | 1-phenyl-ethylamino |
| 16 | —CH$_3$ | 4-methoxyphenyl | isopropylamino |
| 17 | —CH$_3$ | 4-ethoxyphenyl | isopropylamino |
| 18 | —CH$_3$ | 4-fluorophenyl | isopropylamino |
| 19 | —CH$_3$ | 4-methylphenyl | isopropylamino |
| 20 | —CH$_3$ | 4-methylsulfanylphenyl | isopropylamino |
| 21 | —CH$_2$CH$_3$ | 4-methoxyphenyl | 2-hydroxy-1,2-dimethyl-propylamino |
| 22 | —CH$_2$CH$_3$ | 4-ethoxyphenyl | 2-hydroxy-1,2-dimethyl-propylamino |
| 23 | —CH$_2$CH$_3$ | 4-fluorophenyl | 2-hydroxy-1,2-dimethyl-propylamino |
| 24 | —CH$_2$CH$_3$ | 4-methylphenyl | 2-hydroxy-1,2-dimethyl-propylamino |
| 25 | —CH$_2$CH$_3$ | 4-methylsulfanylphenyl | 2-hydroxy-1,2-dimethyl-propylamino |
| 26 | —CH$_2$CH$_3$ | 4-methoxyphenyl | 2-methoxy-1-methyl-ethylamino |

TABLE I-continued

| No. | R | R¹ | R² |
|---|---|---|---|
| 27 | —CH$_2$CH$_3$ | 4-ethoxyphenyl | 2-methoxy-1-methyl-ethylamino |
| 28 | —CH$_2$CH$_3$ | 4-fluorophenyl | 2-methoxy-1-methyl-ethylamino |
| 29 | —CH$_2$CH$_3$ | 4-methylphenyl | 2-methoxy-1-methyl-ethylamino |
| 30 | —CH$_2$CH$_3$ | 4-methylsulfanylphenyl | 2-methoxy-1-methyl-ethylamino |
| 31 | —CH$_2$CH$_3$ | 4-methoxyphenyl | 1-phenyl-ethylamino |
| 32 | —CH$_2$CH$_3$ | 4-ethoxyphenyl | 1-phenyl-ethylamino |
| 33 | —CH$_2$CH$_3$ | 4-fluorophenyl | 1-phenyl-ethylamino |
| 34 | —CH$_2$CH$_3$ | 4-methylphenyl | 1-phenyl-ethylamino |
| 35 | —CH$_2$CH$_3$ | 4-methylsulfanylphenyl | 1-phenyl-ethylamino |
| 36 | —CH$_2$CH$_3$ | 4-methoxyphenyl | isopropylamino |
| 37 | —CH$_2$CH$_3$ | 4-ethoxyphenyl | isopropylamino |
| 38 | —CH$_2$CH$_3$ | 4-fluorophenyl | isopropylamino |
| 39 | —CH$_2$CH$_3$ | 4-methylphenyl | isopropylamino |
| 40 | —CH$_2$CH$_3$ | 4-methylsulfanylphenyl | isopropylamino |
| 41 | —CH(CH$_3$)$_2$ | 4-methoxyphenyl | 2-hydroxy-1,2-dimethyl-propylamino |
| 42 | —CH(CH$_3$)$_2$ | 4-ethoxyphenyl | 2-hydroxy-1,2-dimethyl-propylamino |
| 43 | —CH(CH$_3$)$_2$ | 4-fluorophenyl | 2-hydroxy-1,2-dimethyl-propylamino |
| 44 | —CH(CH$_3$)$_2$ | 4-methylphenyl | 2-hydroxy-1,2-dimethyl-propylamino |
| 45 | —CH(CH$_3$)$_2$ | 4-methylsulfanylphenyl | 2-hydroxy-1,2-dimethyl-propylamino |
| 46 | —CH(CH$_3$)$_2$ | 4-methoxyphenyl | 2-methoxy-1-methyl-ethylamino |
| 47 | —CH(CH$_3$)$_2$ | 4-ethoxyphenyl | 2-methoxy-1-methyl-ethylamino |
| 48 | —CH(CH$_3$)$_2$ | 4-fluorophenyl | 2-methoxy-1-methyl-ethylamino |
| 49 | —CH(CH$_3$)$_2$ | 4-methylphenyl | 2-methoxy-1-methyl-ethylamino |
| 50 | —CH(CH$_3$)$_2$ | 4-methylsulfanylphenyl | 2-methoxy-1-methyl-ethylamino |
| 51 | —CH(CH$_3$)$_2$ | 4-methoxyphenyl | 1-phenyl-ethylamino |
| 52 | —CH(CH$_3$)$_2$ | 4-ethoxyphenyl | 1-phenyl-ethylamino |
| 53 | —CH(CH$_3$)$_2$ | 4-fluorophenyl | 1-phenyl-ethylamino |
| 54 | —CH(CH$_3$)$_2$ | 4-methylphenyl | 1-phenyl-ethylamino |
| 55 | —CH(CH$_3$)$_2$ | 4-methylsulfanylphenyl | 1-phenyl-ethylamino |
| 56 | —CH(CH$_3$)$_2$ | 4-methoxyphenyl | isopropylamino |
| 57 | —CH(CH$_3$)$_2$ | 4-ethoxyphenyl | isopropylamino |
| 58 | —CH(CH$_3$)$_2$ | 4-fluorophenyl | isopropylamino |
| 59 | —CH(CH$_3$)$_2$ | 4-methylphenyl | isopropylamino |
| 60 | —CH(CH$_3$)$_2$ | 4-methylsulfanylphenyl | isopropylamino |
| 61 | —(CH$_2$)$_2$CH$_3$ | 4-methoxyphenyl | 2-hydroxy-1,2-dimethyl-propylamino |
| 62 | —(CH$_2$)$_2$CH$_3$ | 4-ethoxyphenyl | 2-hydroxy-1,2-dimethyl-propylamino |
| 63 | —(CH$_2$)$_2$CH$_3$ | 4-fluorophenyl | 2-hydroxy-1,2-dimethyl-propylamino |
| 64 | —(CH$_2$)$_2$CH$_3$ | 4-methylphenyl | 2-hydroxy-1,2-dimethyl-propylamino |
| 65 | —(CH$_2$)$_2$CH$_3$ | 4-methylsulfanylphenyl | 2-hydroxy-1,2-dimethyl-propylamino |
| 66 | —(CH$_2$)$_2$CH$_3$ | 4-methoxyphenyl | 2-methoxy-1-methyl-ethylamino |
| 67 | —(CH$_2$)$_2$CH$_3$ | 4-ethoxyphenyl | 2-methoxy-1-methyl-ethylamino |
| 68 | —(CH$_2$)$_2$CH$_3$ | 4-fluorophenyl | 2-methoxy-1-methyl-ethylamino |
| 69 | —(CH$_2$)$_2$CH$_3$ | 4-methylphenyl | 2-methoxy-1-methyl-ethylamino |
| 70 | —(CH$_2$)$_2$CH$_3$ | 4-methylsulfanylphenyl | 2-methoxy-1-methyl-ethylamino |
| 71 | —(CH$_2$)$_2$CH$_3$ | 4-methoxyphenyl | 1-phenyl-ethylamino |
| 72 | —(CH$_2$)$_2$CH$_3$ | 4-ethoxyphenyl | 1-phenyl-ethylamino |
| 73 | —(CH$_2$)$_2$CH$_3$ | 4-fluorophenyl | 1-phenyl-ethylamino |
| 74 | —(CH$_2$)$_2$CH$_3$ | 4-methylphenyl | 1-phenyl-ethylamino |
| 75 | —(CH$_2$)$_2$CH$_3$ | 4-methylsulfanylphenyl | 1-phenyl-ethylamino |
| 76 | —(CH$_2$)$_2$CH$_3$ | 4-methoxyphenyl | isopropylamino |
| 77 | —(CH$_2$)$_2$CH$_3$ | 4-ethoxyphenyl | isopropylamino |
| 78 | —(CH$_2$)$_2$CH$_3$ | 4-fluorophenyl | isopropylamino |
| 79 | —(CH$_2$)$_2$CH$_3$ | 4-methylphenyl | isopropylamino |
| 80 | —(CH$_2$)$_2$CH$_3$ | 4-methylsulfanylphenyl | isopropylamino |
| 81 | —(CH$_2$)$_3$CH$_3$ | 4-methoxyphenyl | 2-hydroxy-1,2-dimethyl-propylamino |
| 82 | —(CH$_2$)$_3$CH$_3$ | 4-ethoxyphenyl | 2-hydroxy-1,2-dimethyl-propylamino |
| 83 | —(CH$_2$)$_3$CH$_3$ | 4-fluorophenyl | 2-hydroxy-1,2-dimethyl-propylamino |
| 84 | —(CH$_2$)$_3$CH$_3$ | 4-methylphenyl | 2-hydroxy-1,2-dimethyl-propylamino |
| 85 | —(CH$_2$)$_3$CH$_3$ | 4-methylsulfanylphenyl | 2-hydroxy-1,2-dimethyl-propylamino |
| 86 | —(CH$_2$)$_3$CH$_3$ | 4-methoxyphenyl | 2-methoxy-1-methyl-ethylamino |
| 87 | —(CH$_2$)$_3$CH$_3$ | 4-ethoxyphenyl | 2-methoxy-1-methyl-ethylamino |
| 88 | —(CH$_2$)$_3$CH$_3$ | 4-fluorophenyl | 2-methoxy-1-methyl-ethylamino |
| 89 | —(CH$_2$)$_3$CH$_3$ | 4-methylphenyl | 2-methoxy-1-methyl-ethylamino |
| 90 | —(CH$_2$)$_3$CH$_3$ | 4-methylsulfanylphenyl | 2-methoxy-1-methyl-ethylamino |
| 91 | —(CH$_2$)$_3$CH$_3$ | 4-methoxyphenyl | 1-phenyl-ethylamino |
| 92 | —(CH$_2$)$_3$CH$_3$ | 4-ethoxyphenyl | 1-phenyl-ethylamino |
| 93 | —(CH$_2$)$_3$CH$_3$ | 4-fluorophenyl | 1-phenyl-ethylamino |
| 94 | —(CH$_2$)$_3$CH$_3$ | 4-methylphenyl | 1-phenyl-ethylamino |
| 95 | —(CH$_2$)$_3$CH$_3$ | 4-methylsulfanylphenyl | 1-phenyl-ethylamino |
| 96 | —(CH$_2$)$_3$CH$_3$ | 4-methoxyphenyl | isopropylamino |
| 97 | —(CH$_2$)$_3$CH$_3$ | 4-ethoxyphenyl | isopropylamino |
| 98 | —(CH$_2$)$_3$CH$_3$ | 4-fluorophenyl | isopropylamino |
| 99 | —(CH$_2$)$_3$CH$_3$ | 4-methylphenyl | isopropylamino |
| 100 | —(CH$_2$)$_3$CH$_3$ | 4-methylsulfanylphenyl | isopropylamino |

The compounds which comprise Category I of the present invention can be prepared by the procedure given in Example 1 below as outlined in Scheme I.

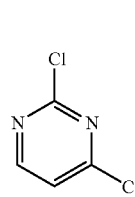
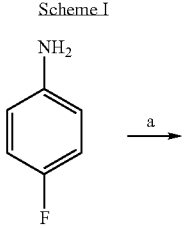

Scheme I

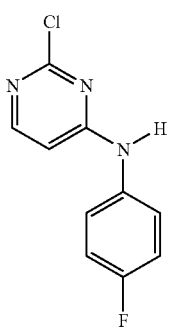

Reagents and conditions: (a) NaHCO₃, EtOH, THF; 65° C. 10 hr.

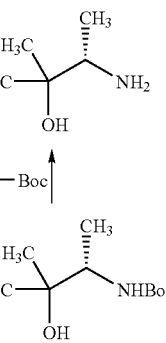
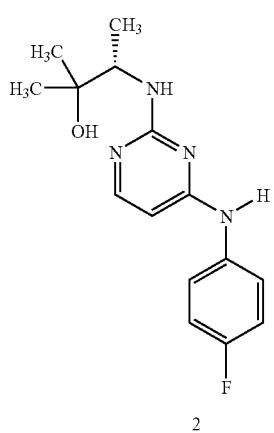

Reagents and conditions: (b) DIPEA, NMP; 130° C. 18 hr.

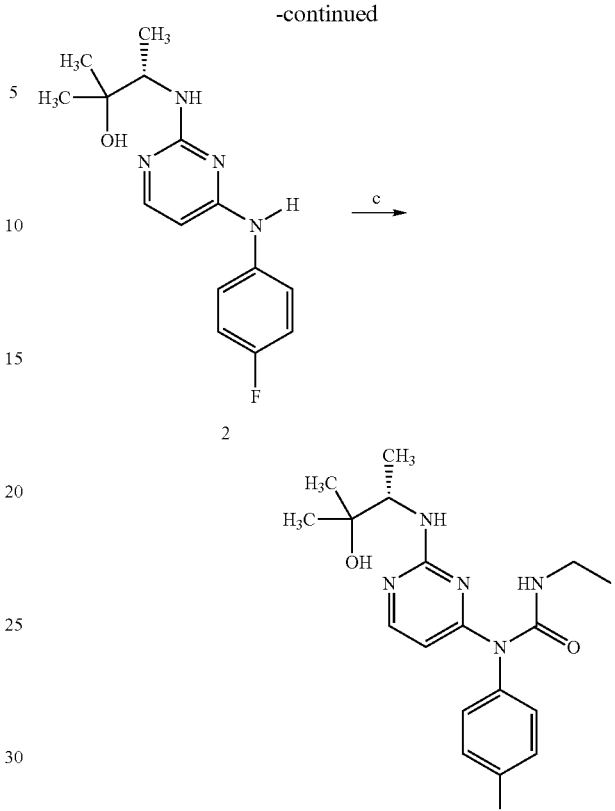

Reagents and conditions: (c) i) TBMSTFA, TEA, dichloroethane; 10° C. to rt, 1.5hr; ii) CH₃CH₂NCO; 50° C. 18 hr; iii) MeOH/H₂O (quench); 5° C.

EXAMPLE 1

1-(4-Fluorophenyl)-1-{2-[(1S)-2-hydroxy-1,2-dimethyl-propylamino]-pyrimidin-4-yl}-3-ethyl-urea (3)

(S)-(2-Hydroxy-1,2-dimethyl-propyl)-carbamic acid tert-butyl ester, which is used in step 2 of the present example and which comprises the $R^2$ unit of the final analog, can be prepared using the method of Konno et. al., *Chem. Pharm. Bull.* (1997), 45, 185, incorporated herein by reference.

Preparation of (2-chloro-pyrimidin-4-yl)-(4-fluoro-phenyl)-amine (2): To a solution of 2,4-dichloropyrimidine (260 g, 1.75 mol) in THF (780 mL) and EtOH (3100 mL) is added NaHCO₃ (244 g, 2.91 mol). To the slurry which results is added 4-fluoroaniline (162 g, 1.46 mol) in one portion and the resulting mixture allowed to warm to 65° C. and held at this temperature for 10 hours. The reaction if not completed in a single day can be cooled over night. Re-heating the next day to 70° C. for an additional 10 hours is usually sufficient for completion of the reaction. The reaction solution is diluted with EtOAc (4.5 L) and washed with water (3×2 L). The combined aqueous layers are extracted with EtOAc (3 L). The combined organic layers are dried over MgSO₄ and filtered. The filter cake is washed with acetone (2×1 L) then with 5% MeOH/acetone (2×500 mL). The filtrate is concentrated until a thick slurry is obtained (ca. 1 L volume), hexane (3.5 L) is added and the solution cooled to about 4° C. for 16 hours. The thick slurry is collected by filtration, washed with hexane (2×500 mL), and dried (20 mmHg, room temperature) to afford 99.43 g (79.3% yield) of the desired product as a white solid. ¹H NMR (300 MHz, CD₃OD) δ 8.06 (d, J=6.0 Hz, 1H), 7.59 (m, 2H), 7.11 (m, 2H), 6.64 (d, J=6.0 Hz, 1H); MS (ESI) m/z 224 (M+1).

Preparation of S-3-[4-(4-fluoro-phenylamino)-pyrimidin-2-ylamino]-2-methyl-butan-2-ol oxalate salt (2): A solution of(S)-(2-Hydroxy-1,2-dimethyl-propyl)-carbamic acid tert-butyl ester (155.6 g, 766 mmol) in CH₂Cl₂ (350 mL) is added to a room temperature solution of trifluoroacetic acid (1350 mL) in CH₂Cl₂ (1 L) over 10-15 minutes or as fast as the gas evolution will allow. The resulting pale brown solution of the deprotected amine is stirred at room temperature an additional 15 minutes and concentrated to yield an oil which is treated with toluene (500 mL) and re-concentrated twice more before being carried forward. The crude amine (S)-2-hydroxy-1,2-dimethyl-propylamine is carefully transferred to a 3 L flask using NMP (320 mL). Diisopropylethyl amine (470 mL) is then added. To this solution is added (2-chloro-pyrimidin-4-yl)-(4-fluoro-phenyl)-amine (111.13 g, 497 mmol) and the reaction is warmed to 130° C. for 18 hours, followed by an additional 18 hours at 135° C. After cooling to room temperature, the reaction solution is diluted with EtOAc (2.5 L) and washed with water (3×1 L). The combined aqueous layers are extracted with EtOAc (1×1 L) and this is combined with the other organic layers. The combined organic layers are washed with saturated aqueous NaCl (1×1 L) and filtered through a 1.2 Kg plug of SiO₂ in a 3 L fritted filter. The plug is eluted with 4 L of each of the following solutions of acetone/EtOAc: 1:19, 1:9, 1:4, 1:1, and 100% acetone. Any fractions containing relatively pure final product are combined. Thin layer chromatograph (TLC) (5% acetone/EtOAc, 0.1% NH₄OH) is used to determine which fractions are enhanced in the final product. The combined fractions are concentrated in vacuo to produce a foamy material which is dissolved in Et₂O (650 mL) and stirred at room temperature. After 1 hour the precipitate which forms can be filtered off. The filtrate is treated with a solution of oxalic acid (89.5 g) in acetone (650 mL) over several minutes. A tacky solid mass particulates after stirring for approximately 1.5 hour and the solid is collected by filtration to afford 126.7 g (70.8% yield) of the desired product as the oxalate salt as a pale violet solid. ¹H NMR (300 MHz, CDCl₃) δ 7.79 (d, J=5.9 Hz, 1H), 7.27 (dd, J=4.8, 9.0 Hz, 2H), 6.98 (t, J=9.0 Hz, 2H), 5.87 (d, J=5.9 Hz, 1H), 4.00-3.90 (m, 1H), 1.23 (s, 3H), 1.16 (m, 3H), 1.15 (s, 3H); MS (ESI) m/z 291 (M+1).

Preparation of 1-(4-fluoro-phenyl)-1-{2-[(1 s)-2-hydroxy-1,2-dimethyl-propylamino]-pyrimidin-4-yl}-3-ethyl-urea (3): S-3-[4-(4-fluoro-phenylamino)-pyrimidin-2-ylamino]-2-methyl-butan-2-ol oxalate salt, 2, (173.1 g, 456 mmol) in dichloroethane (2.7 L) is treated with triethylamine (234 mL, 1.68 mole) at room temperature. Once dissolved, the solution is cooled to about 5° C. in an ice bath and bistrimethylsilyl trifluoroacetamide (445 g, 1.73 mol) is then carefully added in 100 g aliquots. The addition of the silyl compound is accompanied by a slight warming of the solution to about 10° C. The ice bath is removed once the addition is completed and the reaction allowed to stir and warm to room temperature over about 1.5 hours. Ethyl isocyanate (594 mL, 7.52 mol) is then added and the reaction is warmed to 50° C. for about 18 hours. Once the reaction is complete, the solution is treated with toluene (500 mL) and concentrated. The concentrate is cooled to 5° C. then taken up in MeOH (2.5 L) which produces an initial exotherm and then water (100 mL). The solution is stirred at room temperature for 1 hour after which the solvent can be removed to afford a crude oily product which is re-dissolved in CH₂Cl₂ (1.5 L) and stirred for an additional hour. The insoluble material which forms is removed by filtration and the filtrate re-concentrated to a clear oil which is passed through a magnesol plug (3.7 Kg) eluting with CH₂Cl₂ (8 L), 5%, 10%, and 20% acetone/CH₂Cl₂, collecting 4 L fractions. Upgraded (but not pure) fractions by TLC (60% THF/hexane) are collected, concentrated and crystallized from Et₂O to give 78.8 g, 47.9% of white crystals. The mother liquors are purified on SiO₂ (eluting with a THF/hexane gradient) by preparative chromatography to give an additional 18.7 g for a total of 97.5 g, 59.2% of >98% pure material as a white crystal. [α]$_D^{25}$=+3.5 (c=0.43, CH₂Cl₂); ¹H NMR (300 MHz, CDCl₃) δ 9.75 (br s, 1H), 7.88 (d, J=5.9 Hz, 1H), 7.25-7.10 (m, 4H), 5.51 (d, J=5.9 Hz, 1H), 3.93 (br s, 1H), 3.49-3.40 (m, 2H), 1.34-1.27 (m, 12H); MS (ESI) m/z 362 (M+1); HRMS m/z calcd for C₁₈H₂₅FN₅O₂ (MH⁺) 362.1992, found 362.1987.

1-(4-Methoxy-phenyl) 1-{2-[(1S)-2-methoxy-1-methyl-ethylamino]-pyrimidin-4-yl}-3-butyl-urea: ¹H NMR (300 MHz, CDCl₃) δ 9.93 (m, 1H), 7.87 (d, J=5.8 Hz, 1H), 7.13 (d, J=8.8 Hz, 2H), 6.99 (d, J=8.8 Hz, 2H), 5.51 (d, J=6.2 Hz, 1H), 5.32 (br s, 1H), 4.22-3.98 (m, 1H), 3.86 (s, 3H), 3.48 (br d, J=4.8 Hz, 1H), 3.43-3.32 (m, 3H), 3.41 (s, 3H), 3.21-3.06 (m, 1H), 1.68-1.53 (m, 2H), 1.52-1.36 (m, 2H), 1.31 (d, J=6.6 Hz, 3H), 0.98 (t, J=7.3 Hz, 3H); MS (ESI) m/z 388 (M+1).

1-(4-Methoxy-phenyl)-1-{2-[(1S)-2-methoxy-1-methyl-ethylamino]-pyrimidin-4-yl}-3-ethyl-urea: ¹H NMR (300 MHz, CDCl₃) δ 9.93 (br d, J=7.3 Hz, 1H), 8.56 (br s, 1H), 7.63 (d, J=7.3 Hz, 1H), 7.15 (d, J=8.8 Hz, 2H), 7.03 (d, J=8.8 Hz, 2H), 6.04 (d, J=6.6 Hz, 1H), 4.10-4.01 (m, 1H), 3.88 (s, 3H), 3.53-3.26 (m, 5H), 3.38 (s, 3H), 1.30 (d, J=6.6 Hz, 3H), 1.25 (t, J=7.3 Hz, 3H); MS (ESI) m/z 360 (M+1).

1-(4-Methoxyphenyl)-1-{2-[(1S)-2-hydroxy-1,2-dimethylpropylamino]-pyrimidin-4-yl}-3-ethyl-urea: ¹H NMR (300 MHz, CDCl₃) δ 9.58 (br s, 1H), 7.87 (d, J=5.9 Hz, 1H), 7.15 (d, J=9.0 Hz, 2H), 7.01 (d, J=9.0 Hz, 2H), 5.65 (d, J=6.0 Hz, 1H), 3.87 (s, 4H), 3.49-3.40 (m, 2H), 1.33-1.26 (m, 12H); MS (ESI) m/z 374 (M+1).

1-(4-Ethoxyphenyl)-1-{2-[(1S)-2-methoxy-1-methyl-ethylamino]-pyrimidin-4-yl}-3-ethyl-urea: ¹H NMR (300 MHz, CDCl₃) δ 9.89 (br s, 1H), 7.88 (d, J=5.9 Hz, 1H), 7.14 (d, J=9.0 Hz, 1H), 7.14 (d, J=8.9 Hz, 2H), 7.00 (d, J=9.0 Hz, 2H), 5.56 (d, J=5.9 Hz, 1H), 5.50 (br s, 1H), 4.10 (q, J=6.9 Hz, 3H), 3.51 (d, J=4.8 Hz, 2H), 3.44 (s, 5H), 1.47 (t, J=6.9 Hz, 3H), 1.35 (d, J=6.8 Hz, 3H), 1.29 (t, J=7.3 Hz, 3H); MS (ESI) m/z 374 (M+1).

1-(4-Methyl-sulfanylphenyl)-1-{2-[(1S)-2-methoxy-1-methylethylamino]-pyrimidin-4-yl}-3-ethyl-urea: ¹H NMR (300 MHz, CDCl₃) δ 9.90 (br s, 1H), 7.87 (d, J=5.8 Hz, 1H), 7.34 (d, J=8.4 Hz, 2H), 7.14 (d, J=8.4 Hz, 2H), 5.49 (d, J=5.8 Hz, 1H), 5.38 (br s, 1H), 4.10 (br s, 1H), 3.49-3.27 (m, 7H), 2.52 (s, 3H), 1.33-1.19 (m, 6H); MS (ESI) m/z 376 (M+1).

1-(4-Methoxy-phenyl)-1-(2-isopropylamino-pyrimidin-4-yl)-3-ethyl-urea: ¹H NMR (300 MHz, CDCl₃) δ 10.10 (brs, 1H), 7.87 (d, J=5.9 Hz, 1H), 7.15 (d, J=9.0 Hz, 2H), 7.00 (d, J=9.0 Hz, 2H), 5.48 (d, J=5.9 Hz, 1H), 5.03 (br s, 1H), 4.05-3.98 (m, 1H), 3.87 (s, 3H), 3.45 (dq, J=5.3, 7.3 Hz, 1H), 1.32 (d, J=6.6 Hz, 6H), 1.28 (t, J=7.3 Hz, 3H); MS (ESI) m/z 330 (M+1).

1-(4-Methoxy-phenyl)-1-(2-isopropylamino-pyrimidin-4-yl)-3-isopropyl-urea: ¹H NMR (300 MHz, CDCl₃) δ 9.97 (d, J=7.0 Hz, 1H), 7.86 (d, J=6.0 Hz, 1H), 7.15 (d, J=8.8 Hz, 2H), 7.00 (d, J=8.8 Hz, 2H), 5.46 (d, J=5.9 Hz, 1H), 5.03-4.92 (m, 1H), 4.18-3.99 (m, 2H), 3.87 (s, 3H), 1.33 (d, J=6.4 Hz, 6H), 1.29 (d, J=6.6 Hz, 6H); MS (ESI) m/z 344 (M+1).

Further non-limiting examples of compounds according to Category I of the present invention include:
1-(4-Methoxyphenyl)-1-{2-[(1S)-2-methoxy-1-methyl-ethylamino]-pyrimidin-4-yl}-3-methyl-urea;

1-(4-Methoxyphenyl)-1-{2-[(1S)-2-methoxy-1-methyl-ethylamino]-pyrimidin-4-yl}-3-propyl-urea;
1-(4-Methoxyphenyl)-1-{2-[(1s)-2-methoxy-1-methyl-ethylamino]-pyrimidin-4-yl}-3-iso-propyl-urea;
1-(4-Methoxyphenyl)-1-(2-isopropylamino-pyrimidin-4-yl)-3-methyl-urea;
1-(4-Methoxyphenyl)-1-(2-isopropylamino-pyrimidin-4-yl)-3-propyl-urea;
1-(4-Methoxyphenyl)-1-(2-isopropylamino-pyrimidin-4-yl)-3-iso-propyl-urea;
1-(4-Methoxyphenyl)-1-{2-[(1S)-2-hydroxy-1,2-dimethyl-propylamino]-pyrimidin-4-yl}-3-methy-urea;
1-(4-Methoxyphenyl)-1-{2-[(1S)-2-hydroxy-1,2-dimethyl-propylamino]-pyrimidin-4-yl}-3-ethyl-urea;
1-(4-Methoxyphenyl)-1-{2-[(1S)-2-hydroxy-1,2-dimethyl-propylamino]-pyrimidin-4-yl}-3-propyl-urea;
1-(4-Methoxyphenyl)-1-{2-[(1S)-2-hydroxy-1,2-dimethyl-propylamino]-pyrimidin-4-yl}-3-iso-propyl-urea;
1-(4-Methoxyphenyl)-1-{2-[(1S)-1-phenyl-ethylamino]-pyrimidin-4-yl}-3-methyl-urea;
1-(4-Methoxyphenyl)-1-{2-[(1S)-1-phenyl-ethylamino]-pyrimidin-4-yl}-3-ethyl-urea;
1-(4-Methoxyphenyl)-1-{2-[(1S)-1-phenyl-ethylamino]-pyrimidin-4-yl}-3-propyl-urea;
1-(4-Methoxyphenyl)-1-{2-[(1S)-1-phenyl-ethylamino]-pyrimidin-4-yl}-3-iso-propyl-urea;
1-(4-Fluorophenyl)-1-{2-[(1S)-2-methoxy-1-methyl-ethylamino]-pyrimidin-4-yl}-3-methyl-urea;
1-(4-Fluorophenyl)-1-{2-[(1S)-2-methoxy-1-methyl-ethylamino]-pyrimidin-4-yl}-3-propyl-urea;
1-(4-Fluorophenyl)-1-{2-[(1S)-2-methoxy-1-methyl-ethylamino]-pyrimidin-4-yl}-3-iso-propyl-urea;
1-(4-Fluorophenyl)-1-(2-isopropylamino-pyrimidin-4-yl)-3-methyl-urea;
1-(4-Fluorophenyl)-1-(2-isopropylamino-pyrimidin-4-yl)-3-propyl-urea;
1-(4-Fluorophenyl)-1-(2-isopropylamino-pyrimidin-4-yl)-3-iso-propyl-urea;
1-(4-Fluorophenyl)-1-{2-[(1S)-2-hydroxy-1,2-dimethyl-propylamino]-pyrimidin-4-yl}-3-methy-urea;
1-(4-Fluorophenyl)-1-{2-[(1S)-2-hydroxy-1,2-dimethyl-propylamino]-pyrimidin-4-yl}-3-ethyl-urea;
1-(4-Fluorophenyl)-1-{2-[(1S)-2-hydroxy-1,2-dimethyl-propylamino]-pyrimidin-4-yl}-3-propyl-urea;
1-(4-Fluorophenyl)-1-{2-[(1S)-2-hydroxy-1,2-dimethyl-propylamino]-pyrimidin-4-yl}-3-iso-propyl-urea;
1-(4-Fluorophenyl)-1-{2-[(1S)-1-phenyl-ethylamino]-pyrimidin-4-yl}-3-methyl-urea;
1-(4-Fluorophenyl)-1-{2-[(1S)-1-phenyl-ethylamino]-pyrimidin-4-yl}-3$$ -ethyl-urea;
1-(4-Fluorophenyl)-1-{2-[(1S)-1-phenyl-ethylamino]-pyrimidin-4-yl}-3$$ -propyl-urea; and
1-(4-Fluorophenyl)-1-{2-[(1S)-1-phenyl-ethylamino]-pyrimidin-4-yl}-3$$ -iso-propyl-urea.

The compounds which comprise the second aspect of Category I of the present invention are N-(aryl or substituted aryl)-(2-substituted-pyrimidin-4-yl)-N'-substituted alkyl-ureas having the formula:

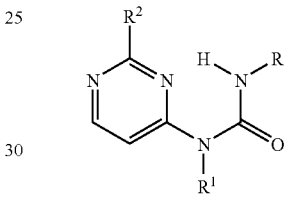

wherein R units are substituted $C_1$-$C_4$ linear or branched alkyl. Non-limiting examples of $R^1$ and $R^2$ are defined herein below in Table II.

TABLE II

| No. | R | $R^1$ | $R^2$ |
|---|---|---|---|
| 101 | —$CH_2OH$ | 4-methoxyphenyl | 2-hydroxy-1,2-dimethyl-propylamino |
| 102 | —$CH_2OH$ | 4-ethoxyphenyl | 2-hydroxy-1,2-dimethyl-propylamino |
| 103 | —$CH_2OH$ | 4-fluorophenyl | 2-hydroxy-1,2-dimethyl-propylamino |
| 104 | —$CH_2OH$ | 4-methylphenyl | 2-hydroxy-1,2-dimethyl-propylamino |
| 105 | —$CH_2OH$ | 4-methylsulfanylphenyl | 2-hydroxy-1,2-dimethyl-propylamino |
| 106 | —$CH_2OH$ | 4-methoxyphenyl | 2-methoxy-1-methyl-ethylamino |
| 107 | —$CH_2OH$ | 4-ethoxyphenyl | 2-methoxy-1-methyl-ethylamino |
| 108 | —$CH_2OH$ | 4-fluorophenyl | 2-methoxy-1-methyl-ethylamino |
| 109 | —$CH_2OH$ | 4-methylphenyl | 2-methoxy-1-methyl-ethylamino |
| 110 | —$CH_2OH$ | 4-methylsulfanylphenyl | 2-methoxy-1-methyl-ethylamino |
| 111 | —$CH_2OH$ | 4-methoxyphenyl | 1-phenyl-ethylamino |
| 112 | —$CH_2OH$ | 4-ethoxyphenyl | 1-phenyl-ethylamino |
| 113 | —$CH_2OH$ | 4-fluorophenyl | 1-phenyl-ethylamino |
| 114 | —$CH_2OH$ | 4-methylphenyl | 1-phenyl-ethylamino |
| 115 | —$CH_2OH$ | 4-methylsulfanylphenyl | 1-phenyl-ethylamino |
| 116 | —$CH_2OH$ | 4-methoxyphenyl | isopropylamino |
| 117 | —$CH_2OH$ | 4-ethoxyphenyl | isopropylamino |
| 118 | —$CH_2OH$ | 4-fluorophenyl | isopropylamino |
| 119 | —$CH_2OH$ | 4-methylphenyl | isopropylamino |
| 120 | —$CH_2OH$ | 4-methylsulfanylphenyl | isopropylamino |
| 121 | —$CH_2OCH_3$ | 4-methoxyphenyl | 2-hydroxy-1,2-dimethyl-propylamino |
| 122 | —$CH_2OCH_3$ | 4-ethoxyphenyl | 2-hydroxy-1,2-dimethyl-propylamino |
| 123 | —$CH_2OCH_3$ | 4-fluorophenyl | 2-hydroxy-1,2-dimethyl-propylamino |
| 124 | —$CH_2OCH_3$ | 4-methylphenyl | 2-hydroxy-1,2-dimethyl-propylamino |
| 125 | —$CH_2OCH_3$ | 4-methylsulfanylphenyl | 2-hydroxy-1,2-dimethyl-propylamino |
| 126 | —$CH_2OCH_3$ | 4-methoxyphenyl | 2-methoxy-1-methyl-ethylamino |
| 127 | —$CH_2OCH_3$ | 4-ethoxyphenyl | 2-methoxy-1-methyl-ethylamino |
| 128 | —$CH_2OCH_3$ | 4-fluorophenyl | 2-methoxy-1-methyl-ethylamino |
| 129 | —$CH_2OCH_3$ | 4-methylphenyl | 2-methoxy-1-methyl-ethylamino |
| 130 | —$CH_2OCH_3$ | 4-methylsulfanylphenyl | 2-methoxy-1-methyl-ethylamino |

TABLE II-continued

| No. | R | R$^1$ | R$^2$ |
|---|---|---|---|
| 131 | —CH$_2$OCH$_3$ | 4-methoxyphenyl | 1-phenyl-ethylamino |
| 132 | —CH$_2$OCH$_3$ | 4-ethoxyphenyl | 1-phenyl-ethylamino |
| 133 | —CH$_2$OCH$_3$ | 4-fluorophenyl | 1-phenyl-ethylamino |
| 134 | —CH$_2$OCH$_3$ | 4-methylphenyl | 1-phenyl-ethylamino |
| 135 | —CH$_2$OCH$_3$ | 4-methylsulfanylphenyl | 1-phenyl-ethylamino |
| 136 | —CH$_2$OCH$_3$ | 4-methoxyphenyl | isopropylamino |
| 137 | —CH$_2$OCH$_3$ | 4-ethoxyphenyl | isopropylamino |
| 138 | —CH$_2$OCH$_3$ | 4-fluorophenyl | isopropylamino |
| 139 | —CH$_2$OCH$_3$ | 4-methylphenyl | isopropylamino |
| 140 | —CH$_2$OCH$_3$ | 4-methylsulfanylphenyl | isopropylamino |
| 141 | —CH$_2$CH$_2$OH | 4-methoxyphenyl | 2-hydroxy-1,2-dimethyl-propylamino |
| 142 | —CH$_2$CH$_2$OH | 4-ethoxyphenyl | 2-hydroxy-1,2-dimethyl-propylamino |
| 143 | —CH$_2$CH$_2$OH | 4-fluorophenyl | 2-hydroxy-1,2-dimethyl-propylamino |
| 144 | —CH$_2$CH$_2$OH | 4-methylphenyl | 2-hydroxy-1,2-dimethyl-propylamino |
| 145 | —CH$_2$CH$_2$OH | 4-methylsulfanylphenyl | 2-hydroxy-1,2-dimethyl-propylamino |
| 146 | —CH$_2$CH$_2$OH | 4-methoxyphenyl | 2-methoxy-1-methyl-ethylamino |
| 147 | —CH$_2$CH$_2$OH | 4-ethoxyphenyl | 2-methoxy-1-methyl-ethylamino |
| 148 | —CH$_2$CH$_2$OH | 4-fluorophenyl | 2-methoxy-1-methyl-ethylamino |
| 149 | —CH$_2$CH$_2$OH | 4-methylphenyl | 2-methoxy-1-methyl-ethylamino |
| 150 | —CH$_2$CH$_2$OH | 4-methylsulfanylphenyl | 2-methoxy-1-methyl-ethylamino |
| 151 | —CH$_2$CH$_2$OH | 4-methoxyphenyl | 1-phenyl-ethylamino |
| 152 | —CH$_2$CH$_2$OH | 4-ethoxyphenyl | 1-phenyl-ethylamino |
| 153 | —CH$_2$CH$_2$OH | 4-fluorophenyl | 1-phenyl-ethylamino |
| 154 | —CH$_2$CH$_2$OH | 4-methylphenyl | 1-phenyl-ethylamino |
| 155 | —CH$_2$CH$_2$OH | 4-methylsulfanylphenyl | 1-phenyl-ethylamino |
| 156 | —CH$_2$CH$_2$OH | 4-methoxyphenyl | isopropylamino |
| 157 | —CH$_2$CH$_2$OH | 4-ethoxyphenyl | isopropylamino |
| 158 | —CH$_2$CH$_2$OH | 4-fluorophenyl | isopropylamino |
| 159 | —CH$_2$CH$_2$OH | 4-methylphenyl | isopropylamino |
| 160 | —CH$_2$CH$_2$OH | 4-methylsulfanylphenyl | isopropylamino |
| 161 | —(CH$_2$)$_2$OCH$_3$ | 4-methoxyphenyl | 2-hydroxy-1,2-dimethyl-propylamino |
| 162 | —(CH$_2$)$_2$OCH$_3$ | 4-ethoxyphenyl | 2-hydroxy-1,2-dimethyl-propylamino |
| 163 | —(CH$_2$)$_2$OCH$_3$ | 4-fluorophenyl | 2-hydroxy-1,2-dimethyl-propylamino |
| 164 | —(CH$_2$)$_2$OCH$_3$ | 4-methylphenyl | 2-hydroxy-1,2-dimethyl-propylamino |
| 165 | —(CH$_2$)$_2$OCH$_3$ | 4-methylsulfanylphenyl | 2-hydroxy-1,2-dimethyl-propylamino |
| 166 | —(CH$_2$)$_2$OCH$_3$ | 4-methoxyphenyl | 2-methoxy-1-methyl-ethylamino |
| 167 | —(CH$_2$)$_2$OCH$_3$ | 4-ethoxyphenyl | 2-methoxy-1-methyl-ethylamino |
| 168 | —(CH$_2$)$_2$OCH$_3$ | 4-fluorophenyl | 2-methoxy-1-methyl-ethylamino |
| 169 | —(CH$_2$)$_2$OCH$_3$ | 4-methylphenyl | 2-methoxy-1-methyl-ethylamino |
| 170 | —(CH$_2$)$_2$OCH$_3$ | 4-methylsulfanylphenyl | 2-methoxy-1-methyl-ethylamino |
| 171 | —(CH$_2$)$_2$OCH$_3$ | 4-methoxyphenyl | 1-phenyl-ethylamino |
| 172 | —(CH$_2$)$_2$OCH$_3$ | 4-ethoxyphenyl | 1-phenyl-ethylamino |
| 173 | —(CH$_2$)$_2$OCH$_3$ | 4-fluorophenyl | 1-phenyl-ethylamino |
| 174 | —(CH$_2$)$_2$OCH$_3$ | 4-methylphenyl | 1-phenyl-ethylamino |
| 175 | —(CH$_2$)$_2$OCH$_3$ | 4-methylsulfanylphenyl | 1-phenyl-ethylamino |
| 176 | —(CH$_2$)$_2$OCH$_3$ | 4-methoxyphenyl | isopropylamino |
| 177 | —(CH$_2$)$_2$OCH$_3$ | 4-ethoxyphenyl | isopropylamino |
| 178 | —(CH$_2$)$_2$OCH$_3$ | 4-fluorophenyl | isopropylamino |
| 179 | —(CH$_2$)$_2$OCH$_3$ | 4-methylphenyl | isopropylamino |
| 180 | —(CH$_2$)$_2$OCH$_3$ | 4-methylsulfanylphenyl | isopropylamino |
| 181 | —(CH$_2$)$_3$CH$_2$OH | 4-methoxyphenyl | 2-hydroxy-1,2-dimethyl-propylamino |
| 182 | —(CH$_2$)$_3$CH$_2$OH | 4-ethoxyphenyl | 2-hydroxy-1,2-dimethyl-propylamino |
| 183 | —(CH$_2$)$_3$CH$_2$OH | 4-fluorophenyl | 2-hydroxy-1,2-dimethyl-propylamino |
| 184 | —(CH$_2$)$_3$CH$_2$OH | 4-methylphenyl | 2-hydroxy-1,2-dimethyl-propylamino |
| 185 | —(CH$_2$)$_3$CH$_2$OH | 4-methylsulfanylphenyl | 2-hydroxy-1,2-dimethyl-propylamino |
| 186 | —(CH$_2$)$_3$CH$_2$OH | 4-methoxyphenyl | 2-methoxy-1-methyl-ethylamino |
| 187 | —(CH$_2$)$_3$CH$_2$OH | 4-ethoxyphenyl | 2-methoxy-1-methyl-ethylamino |
| 188 | —(CH$_2$)$_3$CH$_2$OH | 4-fluorophenyl | 2-methoxy-1-methyl-ethylamino |
| 189 | —(CH$_2$)$_3$CH$_2$OH | 4-methylphenyl | 2-methoxy-1-methyl-ethylamino |
| 190 | —(CH$_2$)$_3$CH$_2$OH | 4-methylsulfanylphenyl | 2-methoxy-1-methyl-ethylamino |
| 191 | —(CH$_2$)$_3$CH$_2$OH | 4-methoxyphenyl | 1-phenyl-ethylamino |
| 192 | —(CH$_2$)$_3$CH$_2$OH | 4-ethoxyphenyl | 1-phenyl-ethylamino |
| 193 | —(CH$_2$)$_3$CH$_2$OH | 4-fluorophenyl | 1-phenyl-ethylamino |
| 194 | —(CH$_2$)$_3$CH$_2$OH | 4-methylphenyl | 1-phenyl-ethylamino |
| 195 | —(CH$_2$)$_3$CH$_2$OH | 4-methylsulfanylphenyl | 1-phenyl-ethylamino |
| 196 | —(CH$_2$)$_3$CH$_2$OH | 4-methoxyphenyl | isopropylamino |
| 197 | —(CH$_2$)$_3$CH$_2$OH | 4-ethoxyphenyl | isopropylamino |
| 198 | —(CH$_2$)$_3$CH$_2$OH | 4-fluorophenyl | isopropylamino |
| 199 | —(CH$_2$)$_3$CH$_2$OH | 4-methylphenyl | isopropylamino |
| 200 | —(CH$_2$)$_3$CH$_2$OH | 4-methylsulfanylphenyl | isopropylamino |

The following are non-limiting examples of compounds which comprise the aspect of Category I of the present invention.

1-(4-Methoxy-phenyl)-1-{2-[(1S)-2-methoxy-1-methyl-ethylamino]-pyrimidin-4-yl}-3-(2-hydroxyethyl)-urea;
1-(4-Methoxy-phenyl)-1-{2-[(1S)-2-methoxy-1-methyl-ethylamino]-pyrimidin-4-yl}-3-(2-methoxyethyl)-urea;
1-(4-Methoxy-phenyl)-1-{2-[(1S)-2-methoxy-1-methyl-ethylamino]-pyrimidin-4-yl}-3-(3-hydroxypropyl)-urea;
1-(4-Methoxy-phenyl)-1-{2-[(1S)-2-methoxy-1-methyl-ethylamino]-pyrimidin-4-yl}-3-(3-methoxypropyl)-urea;
1-(4-Methoxy-phenyl)-1-{2-[(1S)-2-methoxy-1-methyl-ethylamino]-pyrimidin-4-yl}-3-(4-hydroxybutyl)-urea;
1-(4-Methoxy-phenyl)-1-{2-[(1S)-2-methoxy-1-methyl-ethylamino]-pyrimidin-4-yl}-3-(4-methoxybutyl)-urea;
1-(4-Fluoro-phenyl)-1-{2-[(1s)-2-methoxy-1-methyl-ethylamino]-pyrimidin-4-yl}-3-(2-hydroxyethyl)-urea;
1-(4-Fluoro-phenyl)-1-{2-[(1S)-2-methoxy-1-methyl-ethylamino]-pyrimidin-4-yl}-3-(2-methoxyethyl)-urea;
1-(4-Fluoro-phenyl)-1-{2-[(1S)-2-methoxy-1-methyl-ethylamino]-pyrimidin-4-yl}-3-(3-hydroxypropyl)-urea;
1-(4-Fluoro-phenyl)-1-{2-[(1S)-2-methoxy-1-methyl-ethylamino]-pyrimidin-4-yl}-3-(3-methoxypropyl)-urea;
1-(4-Fluoro-phenyl)-1-{2-[(1S)-2-methoxy-1-methyl-ethylamino]-pyrimidin-4-yl}-3-(4-hydroxybutyl)-urea;
1-(4-Fluoro-phenyl)-1-{2-[(1S)-2-methoxy-1-methyl-ethylamino]-pyrimidin-4-yl}-3-(4-methoxybutyl)-urea;
1-(4-Ethoxy-phenyl)-1-{2-[(1S)-2-methoxy-1-methyl-ethylamino]-pyrimidin-4-yl}-3-(2-hydroxyethyl)-urea;
1-(4-Ethoxy-phenyl)-1-{2-[(1S)-2-methoxy-1-methyl-ethylamino]-pyrimidin-4-yl}-3-(2-methoxyethyl)-urea;
1-(4-Ethoxy-phenyl)-1-{2-[(1S)-2-methoxy-1-methyl-ethylamino]-pyrimidin-4-yl}-3-(3-hydroxypropyl)-urea;
1-(4-Ethoxy-phenyl)-1-{2-[(1S)-2-methoxy-1-methyl-ethylamino]-pyrimidin-4-yl}-3-(3-methoxypropyl)-urea;
1-(4-Ethoxy-phenyl)-1-{2-[(1S)-2-methoxy-1-methyl-ethylamino]-pyrimidin-4-yl}-3-(4-hydroxybutyl)-urea;
1-(4-Ethoxy-phenyl)-1-{2-[(1S)-2-methoxy-1-methyl-ethylamino]-pyrimidin-4-yl}-3-(4-methoxybutyl)-urea;
1-(4-Methoxy-phenyl)-1-{2-[(1S)-2-hydroxy-1,2-dimethyl-propylamino]-pyrimidin-4-yl}-3-(2-hydroxyethyl)-urea;
1-(4-Methoxy-phenyl)-1-{2-[(1S)-2-hydroxy-1,2-dimethyl-propylamino]-pyrimidin-4-yl}-3-(2-methoxyethyl)-urea;
1-(4-Methoxy-phenyl)-1-{2-[(1S)-2-hydroxy-1,2-dimethyl-propylamino]-pyrimidin-4-yl}-3-(3-hydroxypropyl)-urea;
1-(4-Methoxy-phenyl)-1-{2-[(1S)-2-hydroxy-1,2-dimethyl-propylamino]-pyrimidin-4-yl}-3-(3-methoxypropyl)-urea;
1-(4-Methoxy-phenyl)-1-{2-[(1S)-2-hydroxy-1,2-dimethyl-propylamino]-pyrimidin-4-yl}-3-(4-hydroxybutyl)-urea;
1-(4-Methoxy-phenyl)-1-{2-[(1S)-2-hydroxy-1,2-dimethyl-propylamino]-pyrimidin-4-yl}-3-(4-methoxybutyl)-urea;
1-(4-Fluoro-phenyl)-1-{2-[(1s)-2-hydroxy-1,2-dimethyl-propylamino]-pyrimidin-4-yl}-3-(2-hydroxyethyl)-urea;
1-(4-Fluoro-phenyl)-1-{2-[(1S)-2-hydroxy-1,2-dimethyl-propylamino]-pyrimidin-4-yl}-3-(2-methoxyethyl)-urea;
1-(4-Fluoro-phenyl)-1-{2-[(1S)-2-hydroxy-1,2-dimethyl-propylamino]-pyrimidin-4-yl}-3-(3-hydroxypropyl)-urea;
1-(4-Fluoro-phenyl)-1-{2-[(1S)-2-hydroxy-1,2-dimethyl-propylamino]-pyrimidin-4-yl}-3-(3-methoxypropyl)-urea;
1-(4-Fluoro-phenyl)-1-{2-[(1S)-2-hydroxy-1,2-dimethyl-propylamino]-pyrimidin-4-yl}-3-(4-hydroxybutyl)-urea;
1-(4-Fluoro-phenyl)-1-{2-[(1 s)-2-hydroxy-1,2-dimethyl-propylamino]-pyrimidin-4-yl}-3-(4-methoxybutyl)-urea;
1-(4-Ethoxy-phenyl)-1-{2-[(1s)-2-hydroxy-1,2-dimethyl-propylamino]-pyrimidin-4-yl}-3-(2-hydroxyethyl)-urea;
1-(4-Ethoxy-phenyl)-1-{2-[(1S)-2-hydroxy-1,2-dimethyl-propylamino]-pyrimidin-4-yl}-3-(2-methoxyethyl)-urea;
1-(4-Ethoxy-phenyl)-1-{2-[(1S)-2-hydroxy-1,2-dimethyl-propylamino]-pyrimidin-4-yl}-3-(3-hydroxypropyl)-urea;
1-(4-Ethoxy-phenyl) 1-{2-[(1S)-2-hydroxy-1,2-dimethyl-propylamino]-pyrimidin-4-yl}-3-(3-methoxypropyl)-urea;
1-(4-Ethoxy-phenyl)-1-{2-[(1S)-2-hydroxy-1,2-dimethyl-propylamino]-pyrimidin-4-yl}-3-(4-hydroxybutyl)-urea;
1-(4-Ethoxy-phenyl)-1-{2-[(1S)-2-hydroxy-1,2-dimethyl-propylamino]-pyrimidin-4-yl}-3-(4-methoxybutyl)-urea;
1-(4-Methoxy-phenyl)-1-[2-(iso-propylamino)-pyrimidin-4-yl]-3-(2-hydroxyethyl)-urea;
1-(4-Methoxy-phenyl)-1-[2-(iso-propylamino)-pyrimidin-4-yl]-3-(2-methoxyethyl)-urea;
1-(4-Methoxy-phenyl)-1-[2-(iso-propylamino)-pyrimidin-4-yl]-3-(3-hydroxypropyl)-urea;
1-(4-Methoxy-phenyl)-1-[2-(iso-propylamino)-pyrimidin-4-yl]-3-(3-methoxypropyl)-urea;
1-(4-Methoxy-phenyl)-1-[2-(iso-propylamino)-pyrimidin-4-yl]-3-(4-hydroxybutyl)-urea;
1-(4-Methoxy-phenyl)-1-[2-(iso-propylamino)-pyrimidin-4-yl]-3-(4-methoxybutyl)-urea;
1-(4-Fluoro-phenyl)-1-[2-(iso-propylamino)-pyrimidin-4-yl]-3-(2-hydroxyethyl)-urea;
1-(4-Fluoro-phenyl)-1-[2-(iso-propylamino)-pyrimidin-4-yl]-3-(2-methoxyethyl)-urea;
1-(4-Fluoro-phenyl)-1-[2-(iso-propylamino)-pyrimidin-4-yl]-3-(3-hydroxypropyl)-urea;
1-(4-Fluoro-phenyl)-1-[2-(iso-propylamino)-pyrimidin-4-yl]-3-(3-methoxypropyl)-urea;
1-(4-Fluoro-phenyl)-1-[2-(iso-propylamino)-pyrimidin-4-yl]-3-(4-hydroxybutyl)-urea;
1-(4-Fluoro-phenyl)-1-[2-(iso-propylamino)-pyrimidin-4-yl]-3-(4-methoxybutyl)-urea;
1-(4-Ethoxy-phenyl)-1-[2-(iso-propylamino)-pyrimidin-4-yl]-3-(2-hydroxyethyl)-urea;
1-(4-Ethoxy-phenyl)-1-[2-(iso-propylamino)-pyrimidin-4-yl]-3-(2-methoxyethyl)-urea;
1-(4-Ethoxy-phenyl)-1-[2-(iso-propylamino)-pyrimidin-4-yl]-3-(3-hydroxypropyl)-urea;
1-(4-Ethoxy-phenyl)-1-[2-(iso-propylamino)-pyrimidin-4-yl]-3-(3-methoxypropyl)-urea;
1-(4-Ethoxy-phenyl)-1-[2-(iso-propylamino)-pyrimidin-4-yl]-3-(4-hydroxybutyl)-urea; and
1-(4-Ethoxy-phenyl)-1-[2-(iso-propylamino)-pyrimidin-4-yl]-3-(4-methoxybutyl)-urea.

Further Categories according to the present invention relate to compounds wherein $R^2$ is a substituted or unsubstituted $C_1$-$C_{10}$ heterocyclic amino unit. A non-limiting example of this Category.

3-Ethyl-1-(4-fluorophenyl)-1-[2-(tetrahydro-pyran-4-ylamino)-pyrimidin-4-yl]-urea: $^1$H NMR (300 MHz, CDCl$_3$) δ 9.77 (m, 1H), 7.92 (d, J=5.9 Hz, 1H), 7.22-7.15 (m, 4H), 5.53 (d, J=5.9 Hz, 2H), 5.10 (br s, 1H), 4.05 (m, 2H), 3.94 (m, 1H), 3.55 (dt, J=11.4, 2.2 Hz, 2H), 3.44 (dq, J=7.3, 5.5 Hz, 2H), 2.10-2.05 (m, 2H), 1.63 (dq, J=11.0, 4.2 Hz, 2H), 1.29 (t, J=7.3 Hz, 3H); MS (ESI) m/z 360 (M+1).

Process

The present invention also relates to a process for preparing the compounds of the present invention.

Aspect 1 of the present invention includes the following steps reagents and procedures. Aspect I is outlined herein below in Scheme II and relates to the conversion of III into product I by way of activated intermediate II.

Scheme II

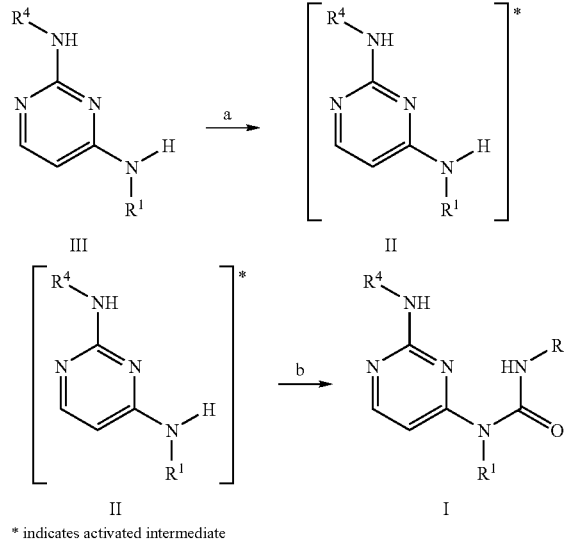

* indicates activated intermediate

Step (a): reacting a 2,4-diaminopyrimidine with an amine activating agent to form in situ an activated 2,4-diaminopyrimidine. Prior to the present invention it was found that 2,4-diaminopyrimidines having the general formula:

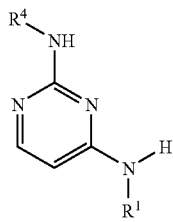

wherein $R^1$ and $R^4$ are defined and detailed herein below, were non-reactive or slow to react with isocyanates. It was surprisingly discovered that treatment of the 2,4-diaminopyrimidine with bistrimethylsilyl trifluoroacetamide thereby forming an activated 2,4-diaminopyrimidine, provided for higher yields and shorter reactions times when the activated 2,4-diaminopyrimidine was treated with an isocyanate. In fact, because of the enhanced reactivity of this activated pyrimidine, lower temperatures can be used, thereby allowing for the use of substituted or unsubstituted $C_1$-$C_{10}$ linear or branched acyclic hydrocarbyl isocyanates. For example, methyl isocyanate, ethyl isocyanate, n-propyl isocyanate, isopropyl isocyanate, and the like, which typically have low boiling points, could be used to form their corresponding 1-(2-substituted amino-pyrimidin-4-yl)-1-(substituted aryl)-3-($C_1$-$C_{10}$ linear or branched alkyl)-ureas utilizing the procedure outlined herein below.

Step (b) of this aspect of the present invention encompassed reacting the activated 2,4-diaminopyrimidine which was formed in situ in step (a) with an isocyanate to form the final tri-substituted urea.

Aspect 2 of the present invention includes the following steps reagents and procedures. Aspect 2 is outlined herein below in Scheme III and relates to the conversion of IV into product I by way of salt IIIa and activated intermediate II.

Scheme III

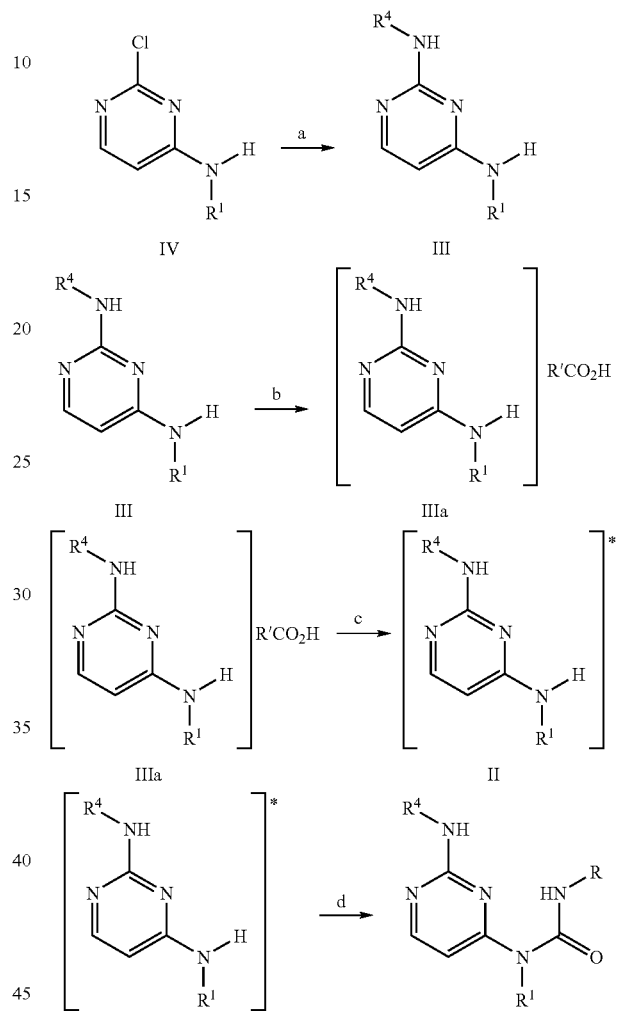

* indicates activated intermediate

Step (a): reacting a 2-chloro-4-aminopyrimidine with an amine to form a 2,4-diaminopyrimidine.

Step (b) of Aspect 2 relates to treating said 2,4-diaminopyrimidine with an acid to form the 2,4-diamino-pyrimidine salt. It has been surprisingly discovered that treating the 2,4-diaminopyrimidine intermediate formed in Step (a) of this aspect with oxalic acid affords increased yields of isolated product and ease of purification.

Step (c) and Step (d) of Aspect 2 of the present invention relate to reacting said 2,4-diaminopyrimidine salt formed in step (b) with bistrimethylsilyl trifluoroacetamide as described herein above to form in situ an activated 2,4-diaminopyrimidine, followed by reacting said activated 2,4-diaminopyrimidine, formed in situ in step (c), with an isocyanate to form the final product, a tri-substituted urea.

Aspect 3 of the present invention includes the following steps reagents and procedures. Aspect 3 is outlined herein below in Scheme IV and relates to the conversion of 2,4-dichloropyrimidine into product I by way of IV, III, salt IIIa and activated intermediate II.

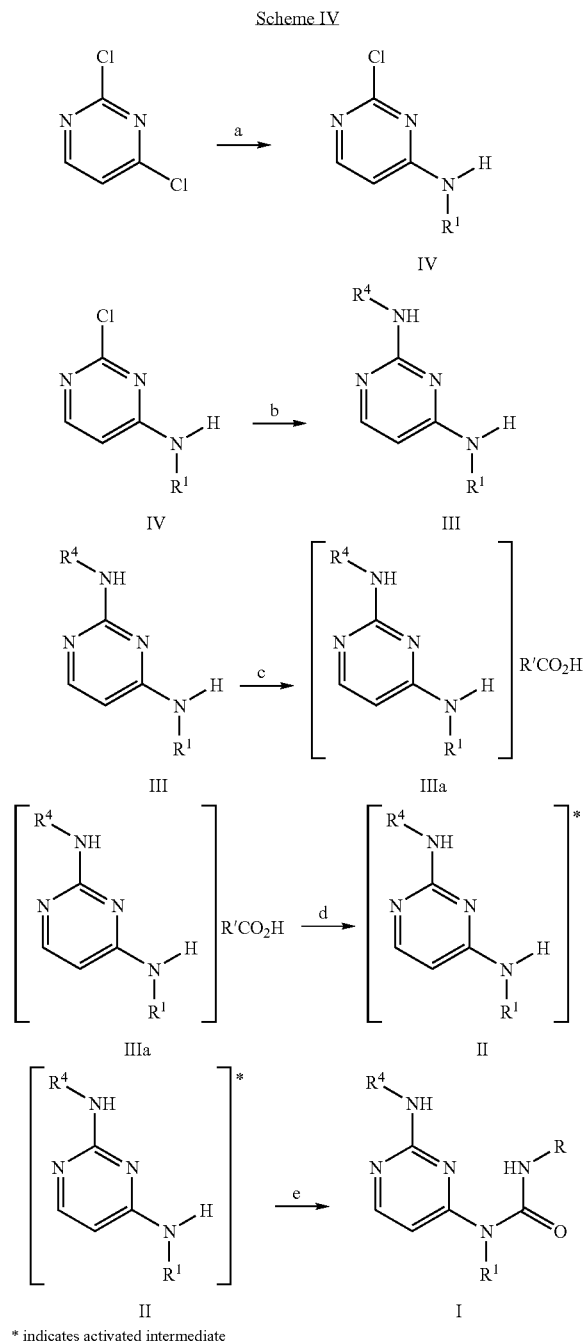

* indicates activated intermediate

Step (a): reacting 2,4-dichloropyrimidine with an amine in the presence of $NaHCO_3$ to form a 2-chloro-4-aminopyrimidine.

It was surprisingly discovered during the course of developing the present invention that the availability, purity, and ease of synthesis of the 2,4-diaminopyrimidine starting material, the starting point for Aspect 1 of the present invention, was predicated on the ability to easily and cost effectively prepare sufficient quantities of the 2-chloro-4-aminopyrimidine starting material of Aspect 2. The 2-chloro-4-aminopyrimidines described herein as part of the present invention are not generally commercially available. In addition, this is the point at which the first of the three urea substituents are added to the core pyrimidine scaffold. High yield, low cost, ease of preparation are important to this step in order for the process described herein to provide a benefit to the consumer. It is well understood the cost of providing pharmaceuticals reflects the cost of starting materials and the process for preparing and purifying the intermediates and final products.

Key to the preparation of the final compounds of the present invention is the surprising discovery that the use of $NaHCO_3$ in step (a) of Aspect 3 leads directly to several process improvements. When $Na_2CO_3$ is used as a base in step (a) of the present process, a large amount of 2,4-di-(substituted or unsubstituted arylamino)pyrimidine is formed. These unwanted by-products are relatively insoluble and are intractable within the reaction matrix. Aside from using up a large portion of the starting amine and therefore requiring an adjustment in the reaction stoichiometry, this material changes the reaction matrix. At times a thick slurry forms which on a larger scale is difficult to work with.

The conditions under which step (b), step (c) and step (d) of Aspect 3 of the present invention are conducted are the same as described herein above for Aspect 1 and Aspect 2 where they apply. As will be understood by those skilled in the art, conditions, stoichiometric amounts, and yields are predicated on the reagents used, the intermediates formed, and the desired final compound.

Compounds listed and described herein above have been found in many instances to exhibit activities ($IC_{50}$ in the cell based assay described herein below or ones which are referenced herein) at a concentration below 1 micromolar ($\lambda M$).

The compounds of the present invention are capable of effectively blocking the inflammatory cytokine production from cells, which thereby allows for the mitigation, alleviation, control, abatement, retardation, or prevention of one or more disease states or syndromes which are related to the extracellular release of one or more cytokines. Inflammatory disease states include those which are related to the following non-limiting examples:

i) Interleukin-1 (IL-1): implicated as the molecule responsible for a large number of disease states, inter alia, rheumatoid arthritis, osteoarthritis, as well as other disease states which relate to connective tissue degradation.

ii) Cycloxygenase-2 (COX-2): inhibitors of cytokine release are proposed as inhibitors of inducible COX-2 expression, which has been shown to be increased by cytokines. M. K. O'Banion et al., *Proc. Natl. Acad. Sci. U.S.A.*, 89, 4888 (1998).

iii) Tumor Necrosis Factor-$\alpha$ (TNF-$\alpha$): This pro-inflammatory cytokine is suggested as an important mediator in many disease states or syndromes, inter alia, rheumatoid arthritis, osteoarthritis, inflammatory bowel disease (IBD), septic shock, cardiopulmonary dysfunction, acute respiratory disease, and cachexia.

iv) The compounds of the present invention have been found to be surprisingly effective in providing analgesia, or otherwise relieving pain in humans and higher mammals.

Each of the disease states or conditions which the formulator desires to treat may require differing levels or amounts of the compounds described herein to obtain a therapeutic level. The formulator can determine this amount by any of the known testing procedures known to the artisan.

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

Related to this aspect are the various precursor of "pro-drug" forms of the analogs of the present invention. It may be desirable to formulate the compounds of the present invention as a chemical species which itself is not active against the cytokine activity described herein, but instead are forms of the present analogs which when delivered to the body of a human or higher mammal will undergo a chemical reaction catalyzed by the normal function of the body, inter alia, enzymes present in the stomach, blood serum, said chemical reaction releasing the parent analog. The term "pro-drug" relates to these species which are converted in vivo to the active pharmaceutical.

Formulations

The present invention also relates to compositions or formulations which comprise the inflammatory cytokine release-inhibiting compounds according to the present invention. In general, the compositions of the present invention comprise:
 a) an effective amount of one or more 1,1,3-tri-substituted ureas and salts thereof according to the present invention which are effective for inhibiting release of inflammatory cytokines; and
 b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Non-limiting examples of compositions according to the present invention include:
 a) from about 0.001 mg to about 1000 mg of one or more 1,1,3-tri-substituted ureas according to the present invention; and
 b) one or more excipient.

Another embodiment according to the present invention relates to the following compositions:
 a) from about 0.01 mg to about 100 mg of one or more 1,1,3-tri-substituted ureas according to the present invention; and
 b) one or more excipient.

A further embodiment according to the present invention relates to the following compositions:
 a) from about 0.1 mg to about 10 mg of one or more 1,1,3-tri-substituted ureas according to the present invention; and
 b) one or more excipient.

The term "effective amount" as used herein means "an amount of one or more 1,1,3-tri-substituted ureas, effective at dosages and for periods of time necessary to achieve the desired result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present invention can be administered as frequently as necessary to achieve a therapeutic amount.

Another aspect of the present invention relates to compositions which provide analgesia, the compositions of the present invention comprise:
 a) an amount of one or more 1,1,3-tri-substituted ureas and salts thereof according to the present invention in an amount effective for providing analgesia;
 b) one or more pharmaceutically acceptable excipients.

As second embodiment of this analgesia-providing aspect of the present invention includes compositions comprising:
 a) an amount of one or more 1,1,3-tri-substituted ureas and salts thereof according to the present invention in an amount effective for providing analgesia;
 b) an effective amount of one or more compounds having pain relief properties; and
 c) one or more pharmaceutically acceptable excipients.

The following are non-limiting examples of compounds having pain relief properties or compounds which are effective in providing relief from pain and which can be suitably combined with the compounds of the present invention:

Acetaminophen, aspirin, difunisal, dipyrone, ibuprofen, naproxen, fenoprofen, fenbufen, ketoprofen, flurbiprofen, indomethacin, ketorolac, diclofenac, floctafenine, piroxicam, celecoxib, and rofecoxib.

The following are non-limiting of adjunct ingredients which may be combined with the compounds of the present invention: Caffeine, compatible amphetamines, compatible antihistamines, compatible antidepressants.

In addition, opioid narcotic analgesics may be combined to form compositions, for example, oxycodone (Percadan, Percacet, Oxycontin, Tylox), pethidine/meperidine (Demerol), methadone (Physeptone, Dolophine), levorphanol (Dromoran, Levodromoran), hydromorphone (Dilaudid), and buprenorphine (Temgesic).

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present invention also relates to compositions or formulations which comprise a precursor or "pro-drug" form of the inflammatory cytokine release-inhibiting compounds according to the present invention. In general, these precursor-comprising compositions of the present invention comprise:
  a) an effective amount of one or more derivatives of the 1,1,3-tri-substituted ureas according to the present invention which act to release in vivo the corresponding analog which is effective for inhibiting release of inflammatory cytokines; and
  b) one or more excipients.

Method of Use

The present invention also relates to a method for controlling the level of one or more inflammation inducing cytokines, inter alia, interleukin-1 (IL-1), Tumor Necrosis Factor-α (TNF-α), interleukin-6 (IL-6), and interleukin-8 (IL-8) and thereby controlling, mediating, or abating disease states affected by the levels of extracellular inflammatory cytokines. The present method comprises the step of administering to a human or higher mammal an effective amount of a composition comprising one or more of the inflammatory cytokine inhibitors according to the present invention.

The present invention also relates to the use of the 1,1,3-tri-substituted ureas according to the present invention in the manufacture of a medicament for the treatment of inflammatory cytokine related disorders. These disorders are described herein above under Inflammatory Disease States.

Because the inflammatory cytokine inhibitors of the present invention can be delivered in a manner wherein more than one site of control can be achieved, more than one disease state can be modulated at the same time. Non-limiting examples of diseases which are affected by control or inhibition of inflammatory cytokine inhibitors, thereby modulating excessive cytokine activity, include osteoarthritis, rheumatoid arthritis, diabetes, human Immunodeficiency virus (HIV) infection.

The present invention further relates to a method for providing analgesia and/or pain relief to humans or higher mammals which comprises the step of administering to said human or higher mammal an effective amount of a 1,1,3-tri-substituted urea described herein above. This method of treatment would also be effective for the treatment of fibromyalgia. This method of treatment may comprise administering to the human or higher mammal a direct amount of one or more analogs. Alternatively, the method comprises the step of administering to said human or higher mammal a pharmaceutical composition which comprises:
  a) an effective amount of one or more 1,1,3-trisubstituted ureas and salts thereof according to the present invention which are effective for inhibiting release of inflammatory cytokines;
  b) an effective amount of one or more compounds having pain relief properties; and
  c) one or more excipients.

The yet further aspect of the present invention relates to methods for reducing inflammatory bowel disease (IBD) in humans and higher mammals, said method comprising the step of administering to a human or high mammal an effective amount of a 1,1,3-tri-substituted urea according to the present invention.

Elevated levels of pro-inflammatory cytokines are implicated in many disease states and inhibition of pro-inflammatory cytokine production offers the opportunity to treat or prevent a wide range of diseases and conditions involving elevated levels of pro-inflammatory cytokines. Cytokines have been linked to acute and chronic inflammatory diseases, such as the inflammatory reaction induced by endotoxin or inflammatory bowel disease (IBD), Crohn's disease and ulcerative colitis, for example, see:
  i) Rankin, E. C. C., et al. 1997, *British J Rheum.* 35:334;
  ii) Stack, W. A., et al. 1997, *The Lancet* 349:521;

both of which are incorporated herein by reference.

An additional aspect of the present invention relates to methods for reducing psoriasis in humans and higher mammals, said method comprising the step of administering to a human or high mammal an effective amount of a 1,1,3-tri-substituted urea according to the present invention. It is well established that the control of cytokine activity is directly related to the formation of psoriasis and inhibition of this activity can be used as a therapy to control this condition. For example, see:

Lamotalos J., et al., "Novel Biological Immunotherapies for Psoriasis." *Expert Opinion Invstigative Drugs*; (2003); 12, 1111-1121.

The present invention, therefore, comprises a method for treating psoriasis in humans which comprises the step of administering to said human a composition which comprises:
  a) an effective amount of one or more 1,1,3-tri-substituted urea and salts thereof according to the present invention which are effective for inhibiting and/or controlling the release of inflammatory cytokines; and
  b) one or more excipients.

The above-described composition is also effective as a therapy against the following disease states, and therefore, provides a method for controlling said disease states:

Congestive Heart Failure[1, 2, 3, 4, 4]; hypertension[5]; chronic obstructive pulmonary disease and septic shock syndrome[6]; adult respiratory distress and asthma[6]; atherosclerosis[9]; muscle degeneration and periodontal diseases; cachexia, Reiter's syndrome, gout, acute synovitis, eating disorders, inter alia, anorexia and bulimia nervosal[11]; fever, malaise, myalgia and headaches[12]. The following are included herein by reference.

1. Han et al., *Trends in Cardiovascular Medicine*, 10:19, (2000);
2. Hunter et al., *New England Journal of Medicine*, 341:1276, (1999);
3. Behr et al. *Circulation*, 102:11-289, (2000);
4. Shimamoto et al, *Circulation:* 102:11-289, (2000);
5. Aukrust et al., *American Journal of Cardiology*, 83:376 (1999);
6. Singh, et al., *Journal of Hypertension*, 9:867 (1996);
7. Dinarello, C. A., *Nutrition* 11:492 (1995);
8. Renzetti, et al. *Inflammation Res.* 46:S143;
9. Elhage, et al., *Circulation* 97:242 (1998);
10. Howells, *Oral Dis.* 1:266 (1995);
11. Holden, et al., *Medical Hypothesis* 47:423 (1996);
12. Beisel, *American Journal of Clinical Nutrition*, 62:813 (1995).

Procedures

The compounds of the present invention can be evaluated for efficacy, for example, measurements of cytokine inhibition constants, $K_i$, and $IC_{50}$ values can be obtained by any method chosen by the formulator.

Non-limiting examples of suitable assays include:
  i) UV-visible substrate enzyme assay as described by L. Al Reiter, *Int. J. Peptide Protein Res.*, 43, 87-96 (1994).
  ii) Fluorescent substrate enzyme assay as described by Thornberry et al., *Nature*, 356, 768-774 (1992).
  iii) PBMC Cell assay as described in U.S. Pat. No. 6,204,261 B1 Batchelor et al., issued Mar. 20, 2001.

Each of the above citations is included herein by reference.

Inhibition of Tumor Necrosis Factor, TNF-α

In addition, Tumor Necrosis Factor, TNF-α, inhibition can be measured by utilizing lipopolysaccharide (LPS) stimulated human monocytic cells (THP-1) as described in:
  i) K. M. Mohler et al., "Protection Against a Lethal Dose of Endotoxin by an Inhibitor of Tumour Necrosis Factor Processing", *Nature*, 370, pp 218-220 (1994).
  ii) U.S. Pat. No. 6,297,381 B1 Cirillo et al., issued Oct. 2, 2001, incorporated by reference and reproduced herein below in relevant portion thereof.

The inhibition of cytokine production can be observed by measuring inhibition of TNF-α in lipopolysaccharide stimulated THP-1 cells. All cells and reagents are diluted in RPMI 1640 with phenol red and L-glutamine, supplemented with additional L-glutamine (total: 4 mM), penicillin and streptomycin (50 units/mL each) and fetal bovine serum (FBS 3%) (GIBCO, all conc. Final). Assay is performed under sterile conditions, only test compound preparation is non-sterile. Initial stock solutions are made in DMSO followed by dilution into RPMI 1640 2-fold higher than the desired final assay concentration. Confluent THP-1 cells (2×10≡cells/mL, final conc.; American Type Culture Company, Rockville, Md.) are added to 96 well polypropylene round bottomed culture plates (Costar 3790; sterile) containing 125 μL test compound (2-fold concentrated) or DMSO vehicle (controls, blanks). DMSO concentration should not exceed 0.2% final. Cell mixture is allowed to preincubate for 15 minutes at 37° C., 5% $CO_2$ prior to stimulation with lipopolysaccharide (LPS, 1 μg/mL final; Sigma L-2630, from *E. coli* serotype 0111.B4; stored as 1 mg/mL stock in endotoxin screened diluted $H_2O$ vehicle at −80° C.). Blanks (unstimulated) receive $H_2O$ vehicle; final incubation volume is 250 μL. Incubation (4 hours) proceeds as described above. Assay is to be terminated by centrifuging plates 5 minutes at room temperature, 1600 rpm (4033 g); supernatants are then transferred to clean 96 well plates and stored at −80° C. until analyzed for human TNF-α by a commercially available ELISA kit (Biosource #KHC3015, Camarillo, Calif.). The calculated $IC_{50}$ value is the concentration of the test compound that caused a 50% decrease in the maximal TNF-α production.

Results for representative compounds according to the present invention are listed in Table below.

TABLE III

| Compound Name | TNF-a $IC_{50}$ (nM) |
|---|---|
| 1-(4-Methoxyphenyl)-1-{2-[(1S)-2-hydroxy-1,2-dimethyl-propylamino]-pyrimidin-4-yl}-3-ethyl-urea | 16 |
| 1-(4-Fluorophenyl)-1-{2-[(1S)-2-hydroxy-1,2-dimethyl-propylamino]-pyrimidin-4-yl}-3-ethyl-urea | 30 |
| 1-(4-Methoxyphenyl)-1-{2-[(1S)-2-methoxy-1-methyl-ethylamino]-pyrimidin-4-yl}-3-ethyl-urea | 666 |
| 1-(4-Ethoxyphenyl)-1-{2-[(1S)-2-methoxy-1-methyl-ethylamino]-pyrimidin-4-yl}-3-ethyl-urea | 276 |
| 1-(4-Methylsulfanylphenyl)-1-{2-[(1S)-2-methoxy-1-methyl-ethylamino]-pyrimidin-4-yl}-3-ethyl-urea | 26 |
| 1-(4-Methoxyphenyl)-1-{2-[(1S)-2-methoxy-1-methyl-ethylamino]-pyrimidin-4-yl}-3-butyl-urea | 324 |
| 1-(4-Fluorophenyl)-1-[2-(tetrahydro-pyran-4-ylamino)-pyrimidin-4-yl]-3-ethyl-urea | 86 |
| 1-(4-Fluorophenyl)-1-[2-(iso-propylamino)-pyrimidin-4-yl]-3-ethyl-urea | 28 |

Iodoacetate Induced Arthritis Test.

The following procedure is used for in vivo testing for arthritis efficacy. Sprague-Dawley male rats weighting 200-225 grams from Harlan (Oregon, Wis.) housed singly in wire cages in sanitary, ventilated animal rooms with controlled temperature, humidity and regular light cycles were used. Rodent chow (Ralston-Purina, Richmond, Ind.) and water were allowed ad libitum. Animals were acclimated for one week before use.

Arthritis was induced by a single intraarticular injection of iodoacetate into the knee joint of rats anesthetized using (3:1) $CO_2/O_2$. A 10 mg/ml concentration of monosodium iodoacetate (IA) (Aldrich Chemical, Milwaukee, Wis.) was prepared using injectable saline as the vehicle. After appropriate anesthesia each rat was positioned on its back and the left leg was flexed 90 degrees at the knee. The patellar ligament was palpated below the patella and the injection was made into this region. Each rat received 0.020 ml intra-articular injection of sodium IA, into the left knee using a glass gas tight syringe with a 27 gauge ¼ inch needle, on day 1 of the study. Care was taken not to advance the needle in too far into the cruciate ligaments.

Groups consisted of animals being dosed orally with 1-(4-fluorophenyl)-1-{2-[(1S)-2-hydroxy-1,2-dimethyl-propylamino]-pyrimidin-4-yl}-3-ethyl-urea (the (S) enatiomer of compound 23 from Table I) @ 25 mg/kg BID (~every 12 hours for 5 days) and Vehicle dosed orally @ 2.5 ml/kg BID (~every 12 hours for 5 days). Following dosing, animals remained on study until humanely sacrificed on day 22 by way of CO2 overdose.

Animals were weighed weekly during this study for health monitoring. Animals were sacrificed on day 22 and the left joint was immediately disarticulated and fixed in 10% buffered formalin for 24 to 48 hours prior to capturing the image.

After fixation, an image of the tibial cartilage surface was captured using an Optimas (Optimas, Media Cybernetics LP, Silver Springs, Mass.) image analysis system. The image was used for grading the severity of damaged cartilage. Three independent observers assessed the damage in a blinded manner using a scale of 0-4 of increasing severity (0=normal; 4=maximum severity).

As described herein above, the compounds of the present invention have been found to be effective as analgesics. One convenient means for evaluating pain and for measuring the effective amount of compound(s) necessary to achieve analgesia and, therefore, provide a means for determining the amount of compound(s) which comprises a pharmaceutical composition of the present invention and the amount of compound(s) necessary for use in the methods described herein, is the Rat Thermal Hyperalgesia Model as described herein below.

The Rat Thermal Hyperalgesia Model, i.e., "Hargreaves Method" [Hargreaves, K., et al., *Pain*, (1988), 32:77-88], is used to determine the level at which the systemic administration of test compounds attenuate the hyperalgesia response subsequent to an intraplantar injection of carrageenan.

Analgesia Test Method:

Sprague-Dawley male rats weighing 100-150 g and housed two per shoebox cage in sanitary, ventilated animal rooms with controlled temperature, humidity and regular light cycles are used. Rodent chow and water were allowed ad libitum. Animals are acclimated for one week before use. All animal use is in accordance with the United States Department of Agriculture guidelines for humane care.

On the first day of study, each animal is acclimated to test equipment and the baseline paw withdrawal latency (PWL) to a radiant heat source is recorded. The following day, animals are orally dosed with vehicle or test compound. Thirty minutes later, each animal receives a 0.1 mL intra plantar injection of carrageenan (1.2% solution, w/v) into the left hind paw. Four hours post-carrageenan injection, animals are returned to the test equipment to determine PWL of the inflamed paw. The animals are then humanely euthanized with an overdose of carbon dioxide. Statistical analysis of data: Change from pre to post PWL for each animal is calculated. Statistical comparison between treatment groups on these two end points are made via an ANCOVA model with treatment terms, as well as pre-treatment measure as baseline covariate.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound, or an enantiomeric or a diastereomeric form, or salt thereof, said compound having the formula:

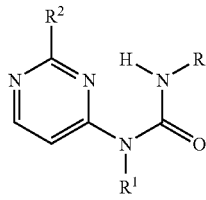

wherein R is substituted or unsubstituted $C_1$-$C_{10}$ linear or branched alkyl; $R^1$ has the formula:

$R^3$ is a unit selected from the group consisting of:
i) substituted or unsubstituted $C_3$-$C_{10}$ carbocyclic;
ii) substituted or unsubstituted $C_6$-$C_{10}$ aryl;
iii) substituted or unsubstituted $C_1$-$C_{10}$ heterocyclic; and
iv) substituted or unsubstituted $C_1$-$C_{10}$ heteroaryl;
$R^2$ has the formula

$R^4$ is a unit selected from the group consisting of:
i) hydrogen;
ii) substituted or unsubstituted $C_1$-$C_{10}$ linear or branched hydrocarbyl;
iii) substituted or unsubstituted $C_3$-$C_{10}$ carbocyclic;
iv) substituted or unsubstituted $C_6$-$C_{10}$ aryl;
v) substituted or unsubstituted $C_1$-$C_{10}$ heterocyclic; and
vi) substituted or unsubstituted $C_1$-$C_{10}$ heteroaryl;
L and $L^1$ are linking groups each of which are independently selected from the group consisting of:
i) —C($R^5$)$_2$—;

ii) —N$R^5$—; and
iii) —O—;
each $R^5$ is hydrogen, $C_1$-$C_4$ linear or branched alkyl; or two $R^5$ units can be taken together to form a carbonyl unit;
the indices x and y are each independently 0 or 1.

2. A compound according to claim 1 wherein R is a $C_1$-$C_4$ alkyl unit chosen from methyl, ethyl, n-propyl, iso-propyl, n-butyl, sec-butyl, iso-butyl, and tert-butyl.

3. A compound according to claim 1 wherein R is a substituted $C_1$-$C_4$ alkyl unit chosen from —CH$_2$OH, —CH$_2$OCH$_3$, —CH$_2$CN, —CH$_2$CH$_2$OH, —CH$_2$CH$_2$OCH$_3$, —CH$_2$CH$_2$CH$_2$OH, —CHOH(CH$_3$)$_2$, —CH$_2$CH$_2$CH$_2$OCH$_3$, —CH$_2$NH$_2$, and —CH$_2$N(CH$_3$)$_2$.

4. A compound according to claim 1 wherein R is a $C_5$-$C_{10}$ linear or methyl branched alkyl unit.

5. A compound according to claim 4 wherein R is chosen from n-pentyl, iso-pentyl, neo-pentyl, n-hexyl, n-heptyl, 2-methylhexyl, 3-methylhexyl, 4-methylhexyl, 2-methylheptyl, n-octyl, n-nonyl, and n-decyl.

6. A compound according to claim 1 wherein $R^1$ has the formula:

the index x is equal to 0 or 1, and $R^3$ is chosen from 4-methoxyphenyl, 4-ethoxyphenyl, 4-fluorophenyl, 4-methylphenyl, and 4-methylsulfanylphenyl.

7. A compound according to claim 1 wherein $R^2$ is chosen from (S)-2-hydroxy-1,2-dimethyl-propylamino, (R)-2-hydroxy-1,2-dimethyl-propylamino, (S)-2-methoxy-1-methyl-ethylamino, (R)-2-methoxy-1-methyl-ethylamino. (S)-1-phenyl-ethylamino, (R)-1-phenyl-ethylamino, and isopropylamino.

8. A compound chosen from:
1-(4-Methoxy-phenyl)-1-{2-[(1S)-2-methoxy-1-methyl-ethylamino]-pyrimidin-4-yl}-3-methyl-urea;
1-(4-Methoxy-phenyl)-1-{2-[(1S)-2-methoxy-1-methyl-ethylamino]-pyrimidin-4-yl}-3-ethyl-urea;
1-(4-Methoxy-phenyl)-1-{2-[(1S)-2-methoxy-1-methyl-ethylamino]-pyrimidin-4-yl}-3-propyl-urea;
1-(4-Methoxy-phenyl)-1-{2-[(1S)-2-methoxy-1-methyl-ethylamino]-pyrimidin-4-yl}-3-iso-propyl-urea;
1-(4-Methoxy-phenyl)-1-{2-[(1S)-2-methoxy-1-methyl-ethylamino]-pyrimidin-4-yl}-3-butyl-urea;
1-(4-Methoxy-phenyl)-1-{2-[(1S)-2-methoxy-1-methyl-ethylamino]-pyrimidin-4-yl}-3-iso-butyl-urea;
1-(4-Methoxy-phenyl)-1-{2-[(1S)-2-methoxy-1-methyl-ethylamino]-pyrimidin-4-yl}-3-sec-butyl-urea;
1-(4-Methoxy-phenyl)-1-{2-[(1S)-2-methoxy-1-methyl-ethylamino]-pyrimidin-4-yl}-3-tert-butyl-urea;
1-(4-Fluoro-phenyl)-1-{2-[(1S)-2-methoxy-1-methyl-ethylamino]-pyrimidin-4-yl}-3-methyl-urea;
1-(4-Fluoro-phenyl)-1-{2-[(1S)-2-methoxy-1-methyl-ethylamino]-pyrimidin-4-yl}-3-ethyl-urea;
1-(4-Fluoro-phenyl)-1-{2-[(1S)-2-methoxy-1-methyl-ethylamino]-pyrimidin-4-yl}-3-propyl-urea;
1-(4-Fluoro-phenyl)-1-{2-[(1S)-2-methoxy-1-methyl-ethylamino]-pyrimidin-4-yl}-3-iso-propyl-urea;
1-(4-Fluoro-phenyl)-1-{2-[(1S)-2-methoxy-1-methyl-ethylamino]-pyrimidin-4-yl}-3-butyl-urea;
1-(4-fluoro-phenyl)-1-{2-[(1S)-2-methoxy-1-methyl-ethylamino]-pyrimidin-4-yl}-3-iso-butyl-urea;
1-(4-fluoro-phenyl)-1-{2-[(1S)-2-methoxy-1-methyl-ethylamino]-pyrimidin-4-yl}-3-sec-butyl-urea;
1-(4-Fluoro-phenyl)-1-{2-[(1S)-2-methoxy-1-methyl-ethylamino]-pyrimidin-4-yl}-3-tert-butyl-urea;
1-(4-Ethoxy-phenyl)-1-{2-[(1S)-2-methoxy-1-methyl-ethylamino]-pyrimidin-4-yl}-3-methyl-urea;

1-(4-Ethoxy-phenyl)-1-{2-[(1S)-2-methoxy-1-methyl-ethylamino]-pyrimidin-4-yl}-3-ethyl-urea;
1-(4-Ethoxy-phenyl)-1-{2-[(1S)-2-methoxy-1-methyl-ethylamino]-pyrimidin-4-yl}-3-propyl-urea;
1-(4-Ethoxy-phenyl)-1-{2-[(1S)-2-methoxy-1-methyl-ethylamino]-pyrimidin-4-yl}-3-iso-propyl-urea;
1-(4-Ethoxy-phenyl)-1-{2-[(1S)-2-methoxy-1-methyl-ethylamino]-pyrimidin-4-yl}-3-butyl-urea;
1-(4-Ethoxy-phenyl)-1-{2-[(1S)-2-methoxy-1-methyl-ethylamino]-pyrimidin-4-yl}-3-iso-butyl-urea;
1-(4-Ethoxy-phenyl)-1-{2-[(1S)-2-methoxy-1-methyl-ethylamino]-pyrimidin-4-yl}-3-sec-butyl-urea;
1-(4-Ethoxy-phenyl)-1-{2-[(1S)-2-methoxy-1-methyl-ethylamino]-pyrimidin-4-yl}-3-tert-butyl-urea;
1-(4-Methyl-phenyl)-1-{2-[(1S)-2-methoxy-1-methyl-ethylamino]-pyrimidin-4-yl}-3-methyl-urea;
1-(4-Methyl-phenyl)-1-{2-[(1S)-2-methoxy-1-methyl-ethylamino]-pyrimidin-4-yl}-3-ethyl-urea;
1-(4-Methyl-phenyl)-1-{2-[(1S)-2-methoxy-1-methyl-ethylamino]-pyrimidin-4-yl}-3-propyl-urea;
1-(4-Methyl-phenyl)-1-{2-[(1S)-2-methoxy-1-methyl-ethylamino]-pyrimidin-4-yl}-3-iso-propyl-urea;
1-(4-Methyl-phenyl)-1-{2-[(1S)-2-methoxy-1-methyl-ethylamino]-pyrimidin-4-yl}-3-buryl-urea;
1-(4-Methyl-phenyl)-1-{2-[(1S)-2-methoxy-1-methyl-ethylamino]-pyrimidin-4-yl}-3-iso-buryl-urea;
1-(4-Methyl-phenyl)-1-{2-[(1S)-2-methoxy-1-methyl-ethylamino]-pyrimidin-4-yl}-3-sec-butyl-urea; and
1-(4-Methyl-phenyl)-1-{2-[(1S)-2-methoxy-1-methyl-ethylamino]-pyrimidin-4-yl}-3-tert-butyl-urea.

9. A composition comprising:
a) an effective amount of a compound, or an enantiomeric or a diastereomeric form, or salt thereof, said compound having the formula:

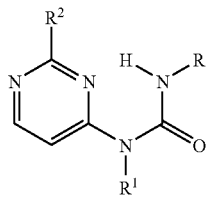

wherein R is substituted or unsubstituted $C_1$-$C_{10}$ linear or branched alkyl;
$R^1$ has the formula:

$R^3$ is a unit selected from the group consisting of:
i) substituted or unsubstituted $C_3$-$C_{10}$ carbocyclic;
ii) substituted or unsubstituted $C_6$-$C_{10}$ aryl;
iii) substituted or unsubstituted $C_1$-$C_{10}$ hererocyclic; and
iv) substituted or unsubstituted $C_1$-$C_{10}$ heteroaryl;
$R^2$ has the formula:

$R^4$ is a unit selected from the group consisting of:
i) hydrogen;
ii) substituted or unsubstituted $C_1$-$C_{10}$ linear or branched hydrocarbyl;
iii) substituted or unsubstituted $C_3$-$C_{10}$ carbocydic;
iv) substituted or unsubstituted $C_6$-$C_{10}$ aryl;
v) substituted or unsubstituted $C_1$-$C_{10}$ heterocyclic; and
vi) substituted or unsubstituted $C_1$-$C_{10}$ heteroaryl;

L and $L^1$ are linking groups each of which are independently selected from the group consisting of:
i) —C($R^5$)$_2$—;
ii) —N$R^5$—; and
iii) —O—;
each $R^5$ is hydrogen, $C_1$-$C_4$ linear or branched alkyl; or two $R^5$ units can be taken together to form a carbonyl unit; the indices x and y are each independently 0 or 1; and
b) one or more pharmaceutically compatible excipients.

10. A composition comprising:
a) an effective amount of one or more compounds according to claim 1; and
b) one or more excipients.

11. A method for treating rheumatoid arthritis or osteoarthritis in humans, said method comprising administering to humans an effective amount of a compound according to claim 1.

12. A process for preparing a tri-substituted urea comprising:
a) reacting a 2,4-diaminopyrimidine having the formula:

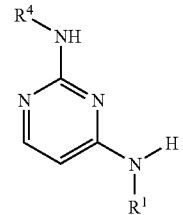

with bis-trimethylsilyl trifluoroacetamide to form in situ an activated 2,4-diamino-pyrimidine; and
b) reacting said activated 2,4-diaminopyrimidine, formed in situ in step (a), with an isocyanate having the formula:

OCN—R to form a tri-substituted urea having the formula:

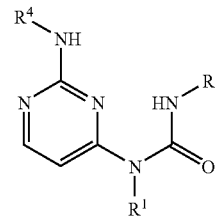

wherein R is substituted or unsubstituted $C_1$-$C_{10}$ linear or branched alkyl;
$R^3$ has the formula:

$R^3$ is a unit selected from the group consisting of:
i) substituted or unsubstituted $C_3$-$C_{10}$ carbocyclic;
ii) substituted or unsubstituted $C_6$-$C_{10}$ aryl;
iii) substituted or unsubstituted $C_1$-$C_{10}$ heterocydic; and
iv) substituted or unsubstituted $C_1$-$C_{10}$ heteroaryl;
$R^4$ is a unit selected from the group consisting of:
i) hydrogen;
ii) substituted or unsubstituted $C_1$-$C_{10}$ linear or branched hydrocarbyl:
iii) substituted or unsubstituted $C_3$-$C_{10}$ carbocyclic;
iv) substituted or unsubstituted $C_6$-$C_{10}$ aryl;

v) substituted or unsubstituted $C_1$-$C_{10}$ heterocyclic; and
vi) substituted or unsubstituted $C_1$-$C_{10}$ heteroaryl;
L is a linking group independently selected from the group consisting of:
i) —C($R^5$)$_2$—;
ii) —N$R^5$—; and
iii) —O—;
each $R^5$ is hydrogen, $C_1$-$C_4$ linear or branched alky; or two $R^5$ units can be taken together to form a carbonyl unit; tile index x is 0 or 1.

13. A process for preparing a tri-substituted urea comprising:
a) reacting 2,4-dichloropyrimidine with an amine having the formula:

in the presence of NaHCO$_3$ wherein $R^1$ is substituted or unsubstituted $C_6$-$C_{10}$ aryl; to form a 2-chloro-4-aminopyrimidine having the formula:

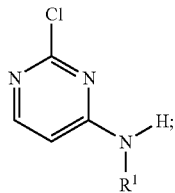

b) reacting said 2-chloro-4-aminopyrimidine with an amine having the formula:

wherein $R^4$ is chosen from:
i) hydrogen;
ii) substituted or unsubstituted $C_1$-$C_{10}$ linear or branched hydrocarbyl;
iii) substituted or unsubstituted $C_3$-$C_{10}$ carbocyclic;
iv) substituted or unsubstituted $C_6$-$C_{10}$ aryl;
v) substituted or unsubstituted $C_1$-$C_{10}$ heterocyclic; and
vi) substituted or unsubstituted $C_1$-$C_{10}$ heteroaryl;
to form a 2,4-diaminopyrimidine having the formula:

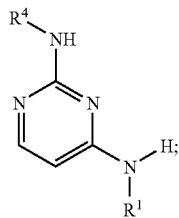

c) treating said 2,4-diaminopyrimidine with oxalic acid to form the 2,4-diaminopyrimidine oxalic acid salt;
d) reacting said 2,4-diaminopyrimidine oxalic acid salt with bis-trimethylsilyl trifluoroacetamide form an activated 2,4-diaminopyrimidine; and
e) reacting said activated 2,4-diaminopyrimidine with an isocyanate having the formula:

R is substituted or unsubstituted $C_1$-$C_{10}$ linear or branched alkyl;
to form a tri-substituted urea having the formula:

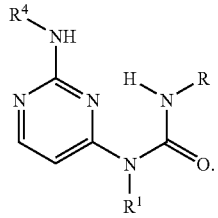

* * * * *

UNITED STATES PATENT AND TRADEMARK OFFICE
CERTIFICATE OF CORRECTION

PATENT NO. : 7,449,474 B2
APPLICATION NO. : 11/111581
DATED : November 11, 2008
INVENTOR(S) : Brugel et al.

It is certified that error appears in the above-identified patent and that said Letters Patent is hereby corrected as shown below:

Column 2
    Line 43, please delete "(Cg)," and insert -- ($C_9$), --.

Column 8
    Line 2, please delete "link R units" and insert -- link $R^4$ units --.

Column 13
    Line 46, please delete "[(1 s)" and insert -- [(1 S) --.

Column 14
    Line 52, please delete "(brs," and insert -- (br s, --.

Column 15
    Line 3, please delete "[(1s)" and insert -- [(1S) --.

Column 16
    Line 14, please delete "3$$ - ethyl-urea;" and insert -- 3 — ethyl urea --.
    Line 16, please delete "3$$ - propyl-urea;" and insert -- 3 — propyl-urea; --.
    Line 18, please delete "3$$ - iso-propyl-urea." and insert
-- 3— *iso*-propyl urea. --.

Column 24
    Line 33, please delete "1 micromolar (λM)." and insert -- 1 micromolar (μM). --.

Column 28
    Line 40, please delete "periodontal diseases" and insert -- periodontal disease[10] --.

UNITED STATES PATENT AND TRADEMARK OFFICE
CERTIFICATE OF CORRECTION

PATENT NO.         : 7,449,474 B2
APPLICATION NO. : 11/111581
DATED              : November 11, 2008
INVENTOR(S)        : Brugel et al.

It is certified that error appears in the above-identified patent and that said Letters Patent is hereby corrected as shown below:

Column 29
　　　Line 30, please delete "(2x10=cells/mL" and insert -- $2 \times 10^5$ cells/mL --.

Signed and Sealed this

Eighteenth Day of August, 2009

David J. Kappos
*Director of the United States Patent and Trademark Office*